United States Patent
Lacombe et al.

(10) Patent No.: US 6,369,084 B1
(45) Date of Patent: Apr. 9, 2002

(54) CARBOXYLIC ACIDS AND ACYLSULFONAMIDES, COMPOSITIONS CONTAINING SUCH COMPOUNDS AND METHODS OF TREATMENT

(75) Inventors: Patrick Lacombe, Montreal; Marc Labelle, Lazare; Rejean Ruel, St-Lazare, all of (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/662,234

(22) Filed: Sep. 14, 2000

Related U.S. Application Data

(60) Provisional application No. 60/153,899, filed on Sep. 14, 1999.

(51) Int. Cl.$^7$ .................. C07D 333/16; C07D 333/24; C07D 409/10; A61K 31/381; A61K 31/44

(52) U.S. Cl. ................. 514/336; 514/183; 514/241; 514/242; 514/252.04; 514/255.05; 514/256; 514/333; 514/340; 514/382; 514/438; 544/179; 544/180; 544/182; 544/238; 544/333; 544/405; 546/268.4; 546/269.1; 546/280.4; 546/281.4; 548/252; 549/59; 549/77; 549/78; 549/79

(58) Field of Search ................. 514/336, 382, 514/438; 549/59, 77, 78, 79; 548/252; 546/280.4

(56) References Cited

U.S. PATENT DOCUMENTS

| 4,829,081 A | 5/1989 | Damon, II et al. ......... 514/460 |
| 4,927,851 A | 5/1990 | Damon, II et al. ......... 514/438 |

FOREIGN PATENT DOCUMENTS

| WO | WO87/02662 | 5/1987 |
| WO | WO96 03380 | 2/1996 |
| WO | WO96/19469 | 6/1996 |
| WO | WO00 20371 | 4/2000 |

*Primary Examiner*—Richard L. Raymond
*Assistant Examiner*—Deepak R. Rao
(74) *Attorney, Agent, or Firm*—Raynard Yuro; Richard C. Billups; David L. Rose

(57) ABSTRACT

This invention encompasses the novel compounds of formula A, which are useful in the treatment of prostaglandin mediated diseases,

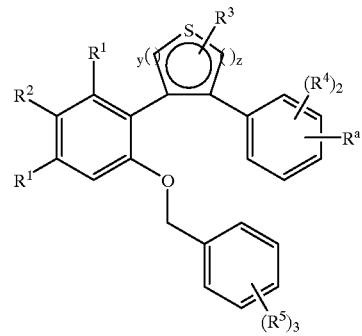

or a pharmaceutically acceptable salt, hydrate or ester thereof. The invention also encompasses certain pharmaceutical compositions and methods for treatment of prostaglandin mediated diseases comprising the use of compounds of formula A.

21 Claims, No Drawings

CARBOXYLIC ACIDS AND ACYLSULFONAMIDES, COMPOSITIONS CONTAINING SUCH COMPOUNDS AND METHODS OF TREATMENT

CROSS-REFERENCE TO RELATED APPLICATIONS

This application claims the benefit of U.S. Provisional Application No. 60/153,899, filed on Sep. 14, 1999.

BACKGROUND OF THE INVENTION

This invention relates to compounds and methods for treating prostaglandin mediated diseases, and certain pharmaceutical compositions thereof. The compounds of the invention are structurally different from NSAIDs and opiates, and are antagonists of the pain and inflammatory effects of E-type prostaglandins.

Two review articles describe the characterization and therapeutic relevance of the prostanoid receptors as well as the most commonly used selective agonists and antagonists: *Eicosanoids: From Biotechnology to Therapeutic Applications,* Folco, Samuelsson, Maclouf, and Velo eds, Plenum Press, New York, 1996, chap. 14, 137–154 and Journal of Lipid Mediators and Cell Signalling, 1996, 14, 83–87. An article from *The British Journal of Pharmacology* (1994, 112, 735–740) suggests that Prostaglandin $E_2$ ($PGE_2$) exerts allodynia through the $EP_1$ receptor subtype and hyperalgesia through $EP_2$ and $EP_3$ receptors in the mouse spinal cord.

Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anticancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects.

In The American Physiological Society (1994, 267, R289-R-294), studies suggest that PGE2-induced hyperthermia in the rat is mediated predominantly through the EP1 receptor. World patent applications WO 96/06822 (Mar. 7, 1996), WO 96/11902 (Apr. 25, 1996) and EP 752421-A1 (Jan. 8, 1997) disclose compounds as being useful in the treatment of prostaglandin mediated diseases.

SUMMARY OF THE INVENTION

The present invention relates to compounds represented by formula A

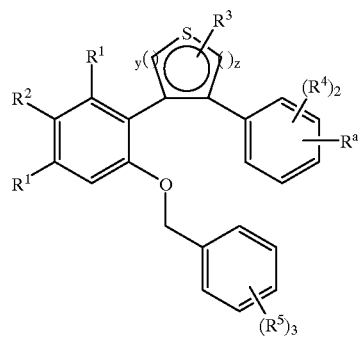

as well as pharmaceutically acceptable salts, hydrates and esters thereof, wherein:

y and z are independently 0–2, such that y+z=2;

$R^a$ is selected from the group consisting of:
1) heteroaryl, wherein heteroaryl is selected from the group consisting of:
   a) furyl,
   b) diazinyl, triazinyl or tetrazinyl,
   c) imidazolyl,
   d) isoxazolyl,
   e) isothiazolyl,
   f) oxadiazolyl,
   g) oxazolyl,
   h) pyrazolyl,
   i) pyrrolyl,
   j) thiadiazolyl,
   k) thiazolyl
   l) thienyl
   m) triazolyl and
   n) tetrazolyl,
said heteroaryl group being optionally substituted with one to three substituents selected from $R^{11}$ and $C_{1-4}$alkyl,
2) —$COR^6$,
3) —$NR^7R^8$,
4) —$SO_2R^9$,
5) hydroxy,
6) $C_{1-6}$alkoxy, optionally substituted with one to three substituents selected from $R^{11}$, and
7) $C_{1-6}$alkyl, $C_{2-6}$alkenyl or $C_{3-6}$cycloalkyl, optionally substituted with one to three substituents selected from $R^{11}$, and further substituted with 1–3 substituents selected from the group consisting of:
   (a) —$COR^6$
   (b) —$NR^7R^8$,
   (c) —$SO_2R^9$,
   (d) hydroxy,
   (e) $C_{1-6}$alkoxy or halo$C_{1-6}$alkoxy, and
   (f) heteroaryl,
such that $R^a$ is positioned on the phenyl ring to which it is bonded in a 1,3 or 1,4 relationship relative to the thienyl group represented in formula A;

each $R^1$, $R^2$, $R^3$, $R^4$ and $R^5$ are independently selected from the group consisting of:
1) hydrogen,
2) halogen,
3) $C_{1-6}$alkyl,
4) $C_{1-6}$alkoxy,
5) $C_{1-6}$alkylthio,
6) nitro, 7) carboxy and 8) CN, wherein items (3)–(5) above are optionally substituted with one or more substituents independently selected from $R^{11}$;

$R^6$ is selected from the group consisting of hydrogen, hydroxy, $C_{1-6}$alkyl, $C_{1-6}$alkoxy and $NR^7R^8$, wherein $C_{1-6}$alkyl or $C_{1-6}$alkoxy are optionally substituted with one or more substituents independently selected from $R^{11}$;

$R^7$ and $R^8$ are independently selected from the group consisting of:

(1) hydrogen, (2) hydroxy, (3) $SO_2R^9$ (4) $C_{1-6}$alkyl, (5) $C_{1-6}$alkoxy, (6) phenyl, (7) naphthyl, (8) furyl, (9) thienyl and

(10) pyridyl, wherein items (4)–(5) above are optionally substituted with one or more substituents independently selected from $R^{11}$, and items (6)–(10) above are optionally substituted with one or more substituents independently selected from $R^{11}$ or $C_{1-4}$alkyl, $R^9$ is selected from the group consisting of (1) hydroxy, (2) $N(R^{10})_2$, (3) $C_{1-6}$alkyl, optionally substituted with one or more substituents independently selected from $R^{11}$, (4) phenyl, (5) naphthyl, (6) furyl, (7) thienyl and (8) pyridyl, wherein items (4)–(8) above are optionally substituted with one or more substituents independently selected from $R^{11}$ or $C_{1-4}$alkyl;

$R^{10}$ is hydrogen or $C_{1-6}$alkyl; and $R^{11}$ is the group consisting of halogen, hydroxy, $C_{1-3}$alkoxy, nitro, $N(R^{10})_2$ and pyridyl.

The invention also encompasses pharmaceutical compositions and methods for treatment of prostaclandin mediated diseases.

DETAILED DESCRIPTION OF THE INVENTION

In one aspect of the invention, the invention encompasses compounds represented by formula A:

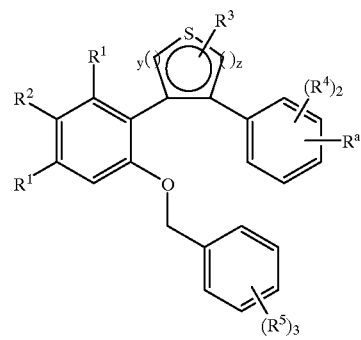

as well as pharmaceutically acceptable salts, hydrates and esters thereof, wherein:

y and z are independently 0–2, such that y+z=2;

$R^a$ is selected from the group consisting of:

1) heteroaryl, wherein heteroaryl is selected from the group consisting of:
   a) furyl,
   b) diazinyl, triazinyl or tetrazinyl,
   c) imidazolyl,
   d) isoxazolyl,
   e) isothiazolyl,
   f) oxadiazolyl,
   g) oxazolyl,
   h) pyrazolyl,
   i) pyrrolyl,
   j) thiadiazolyl,
   k) thiazolyl
   l) thienyl
   m) triazolyl and
   n) tetrazolyl, said heteroaryl group being optionally substituted with one to three substituents selected from $R^{11}$ and $C_{1-4}$alkyl,

2) —$COR^6$,

3) —$NR^7R^8$,

4) —$SO_2R^9$, 5) hydroxy,

6) $C_{1-6}$alkoxy, optionally substituted with 1–3 substituents selected from $R^{11}$, and 7) $C_{1-6}$alkyl, $C_{2-6}$alkenyl or $C_{3-6}$cycloalkyl, optionally substituted with 1–3 substituents selected from $R^{11}$, and further substituted with 1–3 substituents selected from the group consisting of:
   (a) —$COR^6$
   (b) —$NR^7R^8$,
   (c) —$SO_2R^9$,
   (d) hydroxy,
   (e) $C_{1-6}$alkoxy or halo$C_{1-6}$alkoxy, and
   (f) heteroaryl, such that $R^a$ is positioned on the phenyl ring to which it is bonded in a 1,3 or 1,4 relationship relative to the thienyl group represented in formula A;

$R^1$, $R^2$, $R^3$, $R^4$ and $R^5$ are independently selected from the group consisting of:

1) hydrogen, 2) halogen,

3) $C_{1-6}$alkyl,

4) $C_{1-6}$alkoxy,

5) $C_{1-6}$alkylthio, 6) nitro,
7) carboxy and
8) CN, wherein items (3)–(5) above are optionally substituted with one or more substituents independently selected from $R^{11}$;

$R^6$ is selected from the group consisting of hydrogen, hydroxy, $C_{1-6}$alkyl, $C_{1-6}$alkoxy and $NR^7R^8$, wherein $C_{1-6}$alkyl or $C_{1-6}$alkoxy are optionally substituted with one or more substituents independently selected from $R^{11}$;

$R^7$ and $R^8$ are independently selected from the group consisting of:
(1) hydrogen,
(2) hydroxy,
(3) $SO_2R^9$
(4) $C_{1-6}$alkyl,
(5) $C_{1-6}$alkoxy,
(6) phenyl,
(7) naphthyl,
(8) furyl,
(9) thienyl and
(10) pyridyl, wherein items (4)–(5) above are optionally substituted with one or more substituents independently selected from $R^{11}$, and items (6)–(10) above are optionally substituted with one or more substituents independently selected from $R^{11}$ or $C_{1-4}$alkyl, $R^9$ is selected from the group consisting of
(1) hydroxy,
(2) $N(R^{10})_2$,
(3) $C_{1-6}$alkyl, optionally substituted with one or more substituents independently selected from $R^{11}$,
(4) phenyl,
(5) naphthyl,
(6) furyl,
(7) thienyl and
(8) pyridyl, wherein items (4)–(8) above are optionally substituted with one or more substituents independently selected from $R^{11}$ or $C_{1-4}$alkyl;

$R^{10}$ is hydrogen or $C_{1-6}$alkyl; and $R^{11}$ is the group consisting of halogen, hydroxy, $C_{1-3}$alkoxy, nitro, $N(R^{10})_2$ and pyridyl.

An embodiment of the invention that is of particular interest relates to compounds of formula A wherein $R^a$ is selected from the group consisting of: heteroaryl, as originally defined, $COR^6$, wherein $R^6$ is as originally defined, $C_{1-6}$ alkyl and $C_{2-6}$ alkenyl, optionally substituted as originally defined, and $SO_2R^9$ with $R^9$ as originally defined. Within this subset, all other variables are as originally defined.

More particularly, an embodiment of the invention that is of interest relates to a compound of formula A wherein $R^a$ is selected from the group consisting of:

(1)
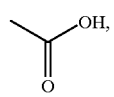

(2)
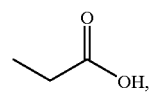

(3)
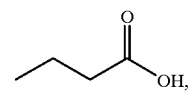

(4)
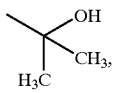

(5)
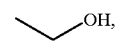

(6)
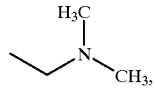

(7)
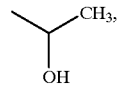

(8)
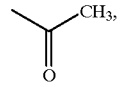

(9)
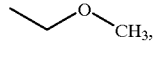

(10)
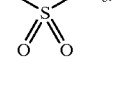

(11)
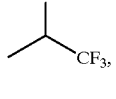

(12)
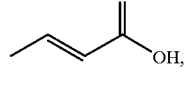

(13)
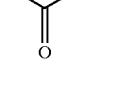

(14)
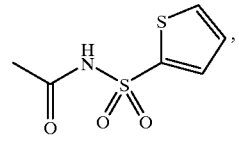

-continued (15)

(16)

(17)

(18)

(19)

(20)

Within this embodiment of the invention, all other variables are as originally defined.

Another embodiment of the invention that is of particular interest relates to compounds of formula A wherein 1–3 of $R^1$ and $R^2$ are selected from the group consisting of halo, $C_{1-4}$ alkyl, $C_{1-4}$ alkoxy, $C_{1-4}$ alkylthio and $NO_2$. Within this subset, all other variables are as originally defined.

Another embodiment of the invention that is of particular interest relates to compounds of formula A wherein each $R^4$ and $R^5$ independently represents a member selected from the group consisting of: H, halo, $C_{1-6}$ alkyl and $C_{1-6}$ alkoxy, said alkyl and alkoxy groups being optionally substituted as originally defined. Within this subset, all other variables are as originally defined.

Another embodiment of the invention that is of particular interest relates to compounds of formula A wherein each $R^3$ independently represents a member selected from the group consisting of: H and halo. Within this subset, all other variables are as originally defined.

Another embodiment of the invention that is of particular interest relates to compounds of formula A wherein one of y and z represents 0 and the other represents 2. Within this subset, all other variables are as originally defined.

An embodiment of the invention that is of more particular interest relates to compounds of formula A wherein $R^a$ is selected from the group consisting of: heteroaryl, as originally defined, $COR^6$, wherein $R^6$ is as originally defined, $C_{1-6}$ alkyl and $C_{2-6}$ alkenyl, optionally substituted as originally defined, and $SO_2R^9$ with $R^9$ as originally defined;

1–3 of $R^1$ and $R^2$ are selected from the group consisting of halo, $C_{1-4}$ alkyl, $C_{1-4}$ alkoxy, $C_{1-4}$ alkylthio and $NO_2$;

each $R^4$ and $R^5$ independently represents a member selected from the group consisting of: H, halo, $C_{1-6}$ alkyl and $C_{1-6}$ alkoxy, said alkyl and alkoxy groups being optionally substituted as originally defined;

each $R^3$ independently represents a member selected from the group consisting of: H and halo;

and one of y and z represents 0 and the other represents 2. Within this subset, all other variables are as originally defined.

Another embodiment of the invention that is of more particular interest relates to compounds of formula A wherein:

$R^a$ is selected from the group consisting of:

(1)

(2)

(3)

(4)

(5)

(6)

(7)

(8)

(9)

(10)

(11)

(12) 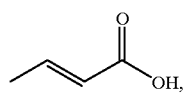

(13) 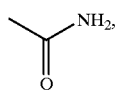

(14) 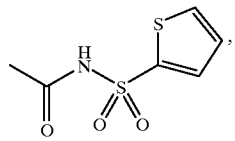

(15) 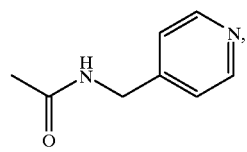

(16) 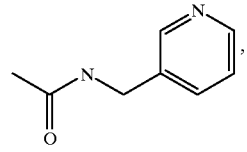

(17) 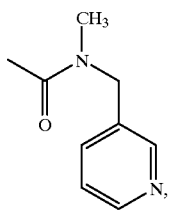

(18) 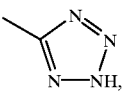

(19) 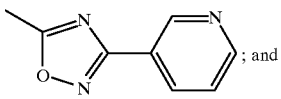 ; and

(20) 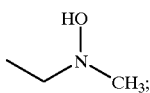

1–3 of $R^1$ and $R^2$ are selected from the group consisting of halo, $C_{1-4}$ alkyl, $C_{1-4}$ alkoxy, $C_{1-4}$ alkylthio and $NO_2$;

each $R^4$ and $R^5$ independently represents a member selected from the group consisting of: H, halo, $C_{1-6}$ alkyl and $C_{1-6}$ alkoxy, said alkyl and alkoxy groups being optionally substituted as originally defined;

each $R^3$ independently represents a member selected from the group consisting of: H and halo;

and one of y and z represents 0 and the other represents 2. Within this subset, all other variables are as originally defined.

Exemplifying the invention are the following compounds:

(a) 4-{3-[2-(Phenylmethoxy)phenyl]-2-thienyl}benzoic acid;
(b) 4-{2-[2-(Phenylmethoxy)phenyl]-3-thienyl}benzoic acid;
(c) 2-(4-{3-[2-(phenylmethoxy)phenyl]-2-thienyl}phenyl) acetic acid;
(d) (4-{3-[2-(phenylmethoxy)phenyl]-2-thienyl}phenyl) methan-1-ol;
(e) 2-(4-{3-[2-(phenylmethoxy)phenyl]-2-thienyl}phenyl) propan-2-ol;
(f) 1-(4-{3-[2-(phenylmethoxy)phenyl]-2-thienyl}phenyl) ethan-1-ol;
(g) 4-{5-bromo-3-[2-(phenylmethoxy)but-2-enyl]-2-thienyl}benzoic acid;
(h) 4-{3-[5-chloro-2-(phenylmethoxy)phenyl]-2-thienyl}benzoic acid;
(i) 3-{3-[5-chloro-2-(phenylmethoxy)phenyl]-2-thienyl}benzoic acid;
(j) 2-chloro-5-{3-[5-chloro-2-(phenylmethoxy)phenyl](2-thienyl)}benzoic acid;
(k) 2-[2-(3-(2H-1,2,3,4-tetraazol-5-yl)phenyl)(3-thienyl)]-4-chloro-1-(phenylmethoxy)benzene;
(l) 5-{3-[5-chloro-2-(phenylmethoxy)phenyl](2-thienyl)}-2-methoxybenzoic acid;
(m) 3-{3-[5-chloro-2-(phenylmethoxy)phenyl](2-thienyl)}-4-fluorobenzoic acid;
(o) 3-{3-[5-chloro-2-(phenylmethoxy)phenyl]-2-thienyl}benzamide;
(p) 2-(3-{3-[5-chloro-2-(phenylmethoxy)phenyl]-2-thienyl}phenyl)acetic acid;
(q) 4-{3-[5-chloro-2-(phenylmethoxy)phenyl](2-thienyl)}-2-methylbenzoic acid;
(r) 4-(3-{2-[(2-chloro-4-fluorophenyl)methoxy]-5-nitrophenyl}-2-thienyl)benzoic acid;
(s) (4-{3-[5-chloro-2-(phenylmethoxy)phenyl](2-thienyl)}phenyl)-N-(3-pyridylmethyl)formamide;
(t) [4-(3-{2-[(2-chloro-4-fluorophenyl)methoxy]-5-nitrophenyl}(2-thienyl))phenyl]-N-(3-pyridylmethyl)formamide;
(u) (4-{3-[5-chloro-2-(phenylmethoxy)phenyl](2-thienyl)}phenyl)-N-(2-thienylsulfonyl)formamide;
(v) 4-(3-{2-[(2,4-difluorophenyl)methoxy]-5-chlorophenyl}(2-thienyl))-3-methylbenzoic acid;
(w) 4-(3-{5-chloro-2-[(4-fluorophenyl)methoxy]phenyl}(2-thienyl))-3-methylbenzoic acid;
(x) 4-{3-[5-chloro-2-(phenylmethoxy)phenyl](2-thienyl)}-3-methylbenzoic acid;
(y) 4-{4-[2-(phenylmethoxy)phenyl]-3-thienyl}benzoic acid;
(z) (4-{4-[2-(phenylmethoxy)phenyl](3-thienyl)}phenyl)-N-(3-pyridylmethyl)formamide;
(aa) 4-[3-(2-{[4-(difluoromethoxy)phenyl]methoxy}-5-chlorophenyl)(2-thienyl)]-3-methylbenzoic acid;
(ab) 4-(3-{2-[(4-carboxyphenyl)methoxy]-5-chlorophenyl}-2-thienyl)benzoic acid;
(ac) 3-(3-{2-[(4-carboxyphenyl)methoxy]-5-chlorophenyl}-2-thienyl)benzoic acid;
(ad) 4-(3-{5-chloro-2-[(2-chloro-4-fluorophenyl)methoxy]phenyl}(2-thienyl))-3-methylbenzoic acid; and
(ae) [4-(3-{5-chloro-2-[(2-chloro-4-fluorophenyl)methoxy]phenyl}(2-thienyl))-3-methylphenyl]-N-(3-pyridylmethyl)formamide.

Another embodiment of the invention is a pharmaceutical composition comprising a compound of formula A in combination with a pharmaceutically acceptable carrier.

Another embodiment of the invention is a method of treating or preventing a prostaglandin mediated disease comprising administering to a mammalian patient in need of such treatment a compound of formula A in an amount which is effective for treating or preventing a prostaglandin mediated disease.

An embodiment of the invention is a method of treating or preventing a prostaglandin mediated disease comprising administering to a mammalian patient in need of such treatment a compound of formula A in an amount which is effective for treating or preventing a prostaglandin mediated disease, wherein the prostaglandin mediated disease is selected from the group consisting of:

(1) pain, fever or inflammation associated with rheumatic fever, influenza or other viral infections, common cold, low back and neck pain, skeletal pain, postpartum pain, dysmenorrhea, headache, migraine, toothache, sprains and strains, myositis, neuralgia, synovitis, arthritis, including rheumatoid arthritis, degenerative joint diseases (osteoarthritis), gout, ankylosing spondylitis, bursitis, burns including radiation and corrosive chemical injuries, sunburns, pain following surgical and dental procedures as well as immune and autoimmune diseases;

(2) cellular neoplastic transformations or metastic tumor growth;

(3) diabetic retinopathy and tumor angiogenesis;

(4) prostanoid-induced smooth muscle contraction associated with dysmenorrhea, premature labor, asthma or eosinophil related disorders;

(5) Alzheimer's disease;

(6) glaucoma;

(7) bone loss;

(8) osteoporosis;

(9) promotion of bone formation;

(10) Paget's disease;

(11) cytoprotection in peptic ulcers, gastritis, regional enteritis, ulcerative colitis, diverticulitis or other gastrointestinal lesions;

(12) GI bleeding and patients undergoing chemotherapy;

(13) coagulation disorders selected from hypoprothrombinemia, haemophilia and other bleeding problems;

(14) kidney disease;

(15) thrombosis;

(16) occlusive vascular disease;

(17) presurgery; and

(18) anti-coagulation.

Another embodiment of the invention is a method of treating or preventing a prostaglandin mediated disease comprising administering to a mammalian patient in need of such treatment a compound of formula A in an amount which is effective for treating or preventing a prostaglandin mediated disease, wherein the prostaglandin mediated disease is selected from the group consisting of: pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases;.

Another embodiment of the invention is a method of treating or preventing a prostaglandin mediated disease comprising administering to a mammalian patient in need of such treatment a compound of formula A in an amount which is effective for treating or preventing a prostaglandin mediated disease, wherein the prostaglandin mediated disease is pain, fever or inflammation associated with dysmenorrhea.

Another embodiment of the invention is a method of treating or preventing a prostaglandin mediated disease comprising administering to a mammalian patient in need of such treatment a compound of formula A in an amount which is effective for treating or preventing a prostaglandin mediated disease, wherein the compound is co-administered with one or more other agents or ingredients.

Another embodiment of the invention is a method of treating or preventing a prostaglandin mediated disease comprising administering to a mammalian patient in need of such treatment a compound of formula A in an amount which is effective for treating or preventing a prostaglandin mediated disease, wherein the compound is co-administered with another agent or ingredient selected from the group consisting of:

(1) an analgesic selected from acetaminophen, phenacetin, aspirin, and a narcotic;

(2) a cyclooxygenase-2 selective nonsteroidal anti-inflammatory drug or a conventional nonsteroidal anti-inflammatory drug;

(3) caffeine;

(4) an $H_2$-antagonist;

(5) aluminum or magnesium hydroxide;

(6) simethicone;

(7) a decongestant selected from phenylephrine, phenylpropanolamine, pseudophedrine, oxymetazoline, ephinephrine, naphazoline, xylometazoline, propylhexedrine, or levo-desoxyephedrine;

(8) an antiitussive selected from codeine, hydrocodone, caramiphen, carbetapentane and dextramethorphan;

(9) another prostaglandin ligand selected from misoprostol, enprostil, rioprostil, ornoprostol and rosaprostol; a diuretic; and

(10) a sedating or non-sedating antihistamine.

Examples of COX-2 inhibitors are disclosed in U.S. Pat. Nos. 5,474,995; 5,633,272; and 5,466,823; and in WO 96/25405, WO 97/38986, WO 98/03484, WO 97/14691, and WO 95/0051.

Another embodiment of the invention is a method of treating or preventing a prostaglandin mediated disease comprising administering to a mammalian patient in need of such treatment a compound of formula A in an amount which is effective for treating or preventing a prostaglandin mediated disease, wherein the compound is co-administered with a cyclooxygenase-2 selective nonsteroidal anti-inflammatory drug or a conventional nonsteroidal anti-inflammatory drug.

Another embodiment of the invention is a method of treating or preventing a prostaglandin mediated disease comprising administering to a mammalian patient in need of such treatment a compound of formula A in an amount which is effective for treating or preventing a prostaglandin mediated disease, wherein the compound is co-administered with a conventional nonsteroidal anti-inflammatory drug selected from the group consisting of: aspirin, ibuprofen, naproxen, and ketoprofen.

Another embodiment of the invention is a method of treating or preventing a prostaglandin mediated disease comprising administering to a mammalian patient in need of such treatment a compound of formula A in an amount which is effective for treating or preventing a prostaglandin mediated disease, wherein the compound is co-administered with a cyclooxygenase-2 selective nonsteroidal anti-inflammatory drug selected from rofecoxib and celecoxib.

The invention is described using the following definitions unless otherwise indicated.

The term "halogen" or "halo" includes F, Cl, Br, and I.

The term "alkyl" means linear, branched or cyclic structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

"Alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

"Alkylthio" means alkylthio groups having the indicated number of carbon atoms of a straight, branched or cyclic configuration. $C_{1-6}$alkylthio, for example, includes methylthio, propylthio, isopropylthio, etc. By way of illustration, the propylthio group signifies —$SCH_2CH_2CH_3$.

"Haloalkyl" means an alkyl group, including linear, branched or cyclic structures, of the indicated number of carbon atoms in which one or more hydrogen atoms have been replaced by halogen atoms, with up to complete substitution of all hydrogen atoms with halo groups. $C_{1-6}$haloalkyl, for example, includes —$CF_3$, —$CF_2CF_3$ and the like.

"Haloalkoxy" means an alkoxy group, including linear, branched or cyclic structures, of the indicated number of carbon atoms in which one or more hydrogen atoms have been replaced by halogen atoms, with up to complete substitution of all hydrogen atoms with halo groups. $C_{1-6}$haloalkoxy, for example, includes —$OCF_3$, —$OCF_2CF_3$ and the like.

"Alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

For purposes of this specification, the following abbreviations have the indicated meanings:

| | |
|---|---|
| BOC = | t-butyloxycarbonyl |
| CBZ = | carbobenzoxy |
| DCC = | 1,3-dicyclohexylcarbodiimide |
| DIBAL = | diisobutyl aluminum hydride |
| DIEA = | N,N-diisoproylethylamine |
| DMAP = | 4-(dimethylamino)pyridine |
| EDCI = | 1-(3-dimethylaminopropyl)-3-ethylcarbodiimide hydrochloride |
| EDTA = | ethylenediaminetetraacetic acid, tetrasodium salt hydrate |
| FAB = | fast atom bombardment |
| FMOC = | 9-fluorenylmethoxycarbonyl |
| HMPA = | hexamethylphosphoramide |
| HATU = | O-(7-Azabenzotriazol-l-yl)N,N,N',N'-tetramethyluronium hexafluorophosphate |
| HOBt = | 1-hydroxybenzotriazole |
| HRMS = | high resolution mass spectrometry |
| ICBF = | isobutyl chloroformate |
| KHMDS = | potassium hexamethyldisilazane |
| LDA = | lithium diisopropylamide |
| MCPBA = | metachloroperbenzoic acid |

-continued

| | |
|---|---|
| Ms = | methanesulfonyl = mesyl |
| MsO = | methanesulfonate = mesylate |
| NBS = | N-bromosuccinimide |
| NMM = | 4-methylmorpholine |
| PCC = | pyridinium chlorochromate |
| PDC = | pyridinium dichromate |
| Ph = | phenyl |
| PPTS = | pyridinium p-toluene sulfonate |
| pTSA = | p-toluene sulfonic acid |
| r.t. = | room temperature |
| rac. = | racemic |
| TfO = | trifluoromethanesulfonate = triflate |
| TLC = | thin layer chromatography |

| Alkyl group abbreviations | |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |

Unless otherwise specified, when a nitrogen atom appears in a structure, hydrogen atoms are implied to satisfy the valence requirement.

The pharmaceutical compositions of the present invention comprise a compound of formula A as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of formula A are meant to also include the pharmaceutically acceptable salts.

The magnitude of prophylactic or therapeutic dose of a compound of formula A will, of course, vary with the nature and the severity of the condition to be treated and with the particular compound of formula A and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably about 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from about 0.5 mg to 5 g of active agent compounded with an appropriate and convenient amount of carrier material which may vary from about 5 to about 95 percent of the total composition. Dosage unit forms will generally contain between from about 1 mg to about 2 g of an active ingredient, typically 25 mg, 50 mg, 100 mg, 200 mg, 300 mg, 400 mg, 500 mg, 600 mg, 800 mg, or 1000 mg.

For the treatment of any of the above mentioned diseases and conditions, the compound of formula A may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula A may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula A are employed. (For purposes of this application, topical application shall include mouth washes and gargles.) Topical formulations may generally be comprised of a pharmaceutical carrier, cosolvent, emulsifier, penetration enhancer, preservative system, and emollient.

The ability of the compounds of formula A to interact with prostaglandin receptors makes them useful for preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent, or ameliorate in mammals and especially in humans: Pain, fever and inflammation of a variety of conditions including rheumatic fever, symptoms associated with influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases. In addition, such a compound may inhibit cellular neoplastic transformations and metastic tumor growth and hence can be used in the treatment of cancer. Compounds of formula A may also be of use in the treatment and/or prevention prostaglandin-mediated proliferation disorders such as may occur in diabetic retinopathy and tumor angiogenesis. Compounds of formula A will also inhibit prostanoid-induced smooth muscle contraction by antagonizing contractile prostanoids or mimicking relaxing prostanoids and hence may be use in the treatment of dysmenorrhea, premature labor, asthma and eosinophil related disorders. It will also be of use in the treatment of Alzheimer's disease, the treatment of glaucoma, for the prevention of bone loss (treatment of osteoporosis) and for the promotion of bone formation (treatment of fractures) and other bone diseases such as Paget's disease.

By virtue of its prostanoid or prostanoid antagonist activity, a compound of formula A will prove useful as an alternative to conventional non-steroidal anti-inflammatory drugs (NSAID'S) particularly where such non-steroidal anti-inflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; thrombosis, occlusive vascular diseases; those prior to surgery or taking anti-coagulants. Compounds of formula A will also be useful as a cytoprotective agent for patients under chemotherapy.

Compounds of formula A will be useful as a partial or complete substitute for conventional antuinflammatory or analgesic compounds in preparations wherein they are presently co-administered with other agents or ingredients. Thus in further aspects, the invention encompasses pharmaceutical compositions for treating prostaglandin E2 mediated diseases as defined above comprising a non-toxic therapeutically effective amount of the compound of formula A as defined above and one or more ingredients such as another pain reliever including acetaminophen or phenacetin; a COX-2 selective inhibiting agent; a conventional NSAID; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; another prostaglandin ligand including misoprostol, enprostil, rioprostil, ornoprostol or rosaprostol; a diuretic; a sedating or non-sedating antihistamine. In addition, the invention encompasses a method of treating prostaglandin E2 mediated diseases comprising: administration to a patient in need of such treatment a non-toxic therapeutically effective amount of the compound of formula A, optionally co-administered with one or more of such ingredients as listed immediately above.

METHODS OF SYNTHESIS

Compounds of the present invention can be prepared according to the following methods.

Preparation of Common Intermediates

As illustrated in Scheme 1, the thiophene derivative (3) is prepared by reacting 2-bromophenylbenzyl ether (1) with thiophene 3-boronic acid (2) under conditions such as palladium catalyzed Suzuki's cross coupling reaction. The thiophene derivative (3) can then be brominated selectively at the 2 position using reagents such as NBS in THF/H$_2$O (50:1). Subsequent Suzuki's cross coupling reaction with the desired boronic acid (5) affords the desired benzoic acid derivative (6).

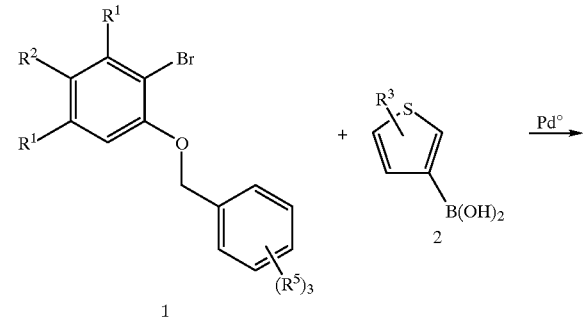

Scheme 1

-continued

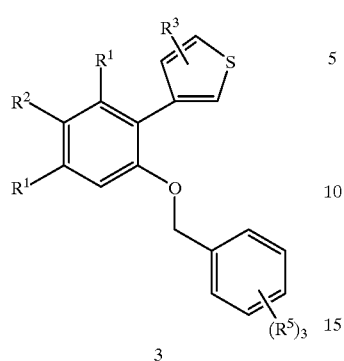

3

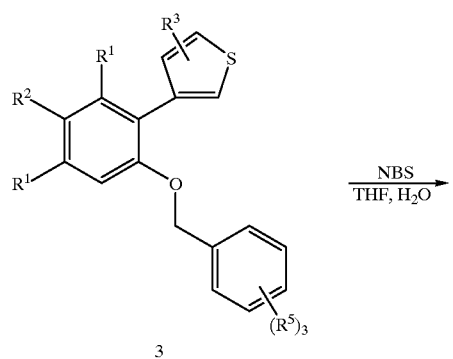

3

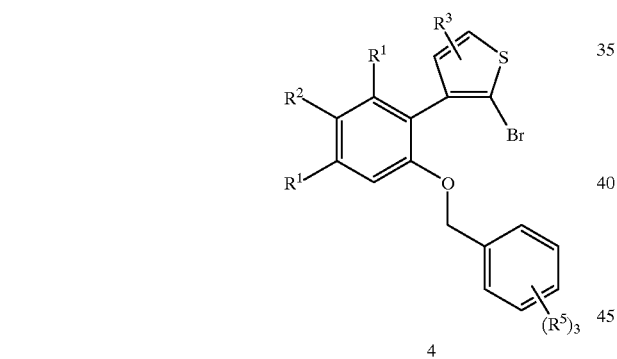

4

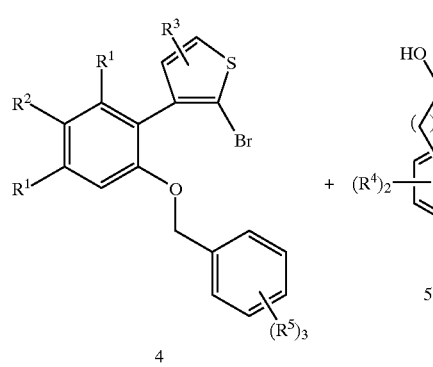

4

-continued

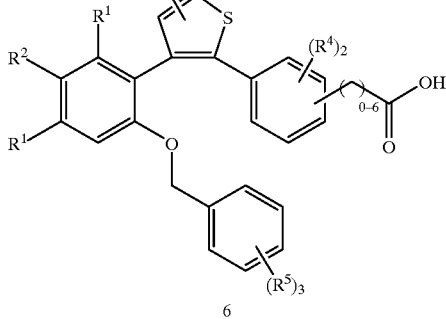

6

In a similar fashion, the thiophene isomers (13) can be prepared as shown in Scheme 2 by submitting 3-bromothiophene compounds (7) under palladium catalyzed Suzuki's cross coupling with the desired boronic acid (8) to give the derivative (9), which is then brominated selectively at the 2 position using reagents such as NBS in THF/H$_2$O (50:1). Finally, palladium catalyzed Suzuki's cross coupling reaction between the bromo derivative (10) and the desired boronic acid (11) followed by basic hydrolysis of the ester lead to the desired product (13).

Scheme 2

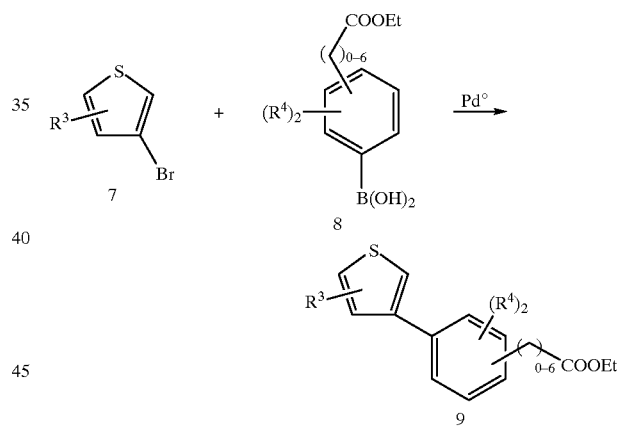

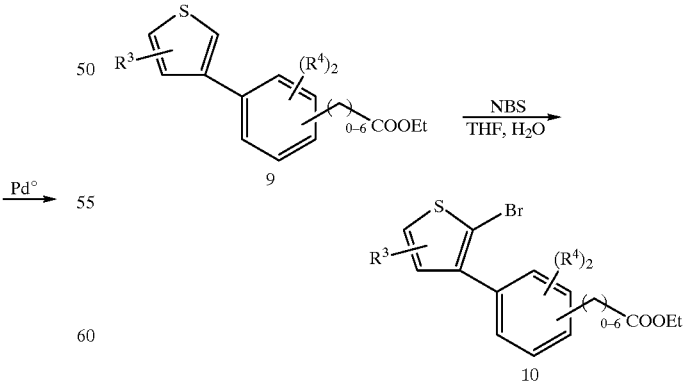

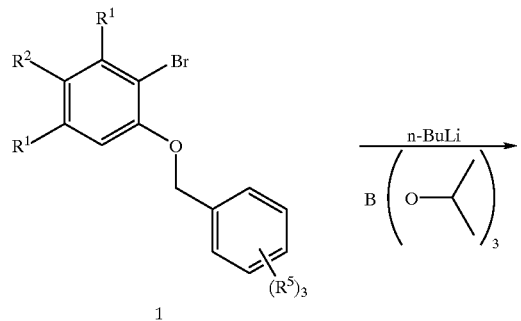
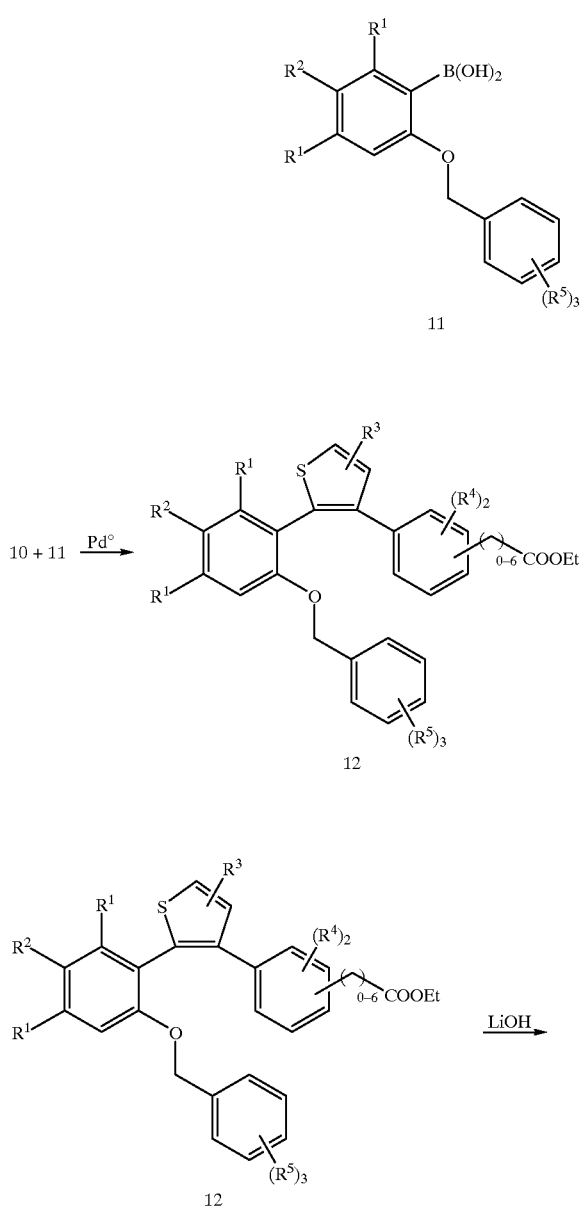
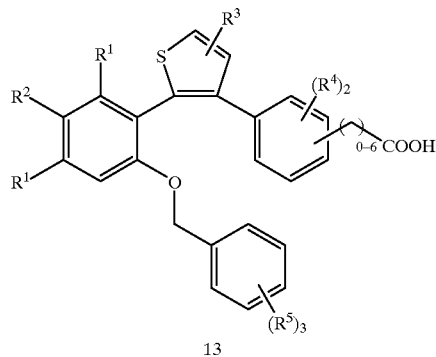
The other thiophene isomer (17) is prepared via a multi-step sequence as shown in Scheme 3. 3,4-dibromothiophene (14) is reacted with the boronic acid (8) to yield the derivative (15), which is once submitted to palladium catalyzed Suzuki's cross coupling reaction with the desired boronic acid (11) followed by basic hydrolysis to afford the desired material (17).
Scheme 3
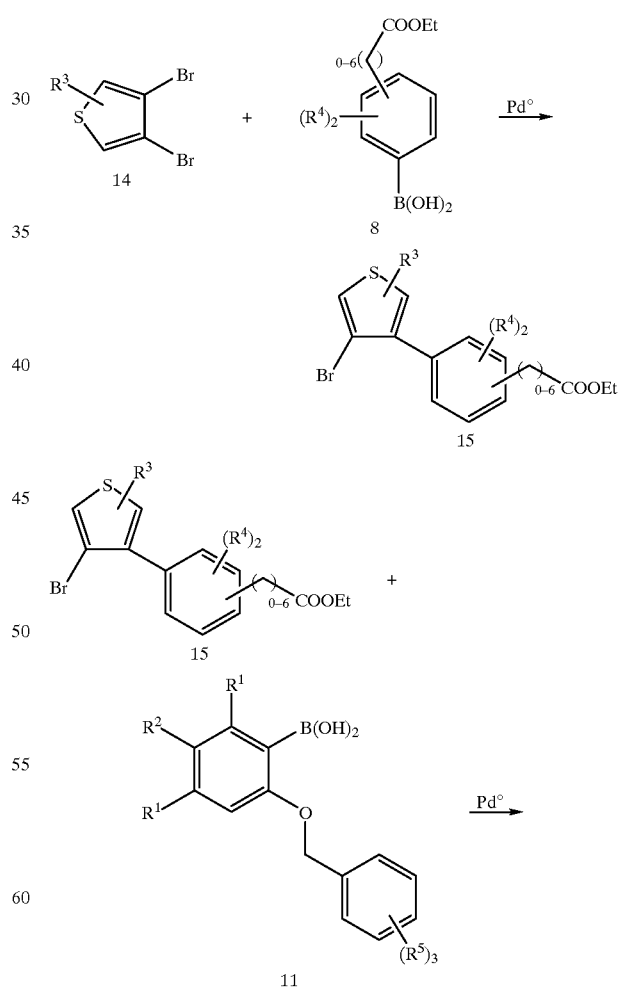

-continued

REPRESENTATIVE COMPOUNDS

Table 1 illustrates compounds of formula A which are representative of the present invention.

TABLE 1

| COMPOUND | EXAMPLE |
|---|---|
| (structure) | 1 |
| (structure) | 2 |
| (structure) | 3 |
| (structure) | 4 |

TABLE 1-continued

| COMPOUND | EXAMPLE |
|---|---|
| (structure) | 5 |
| (structure) | 6 |
| (structure) | 7 |
| (structure) | 8 |
| (structure) | 9 |
| (structure) | 10 |
| (structure) | 11 |
| (structure) | 12 |
| (structure) | 13 |

TABLE 1-continued

| COMPOUND | EXAMPLE |
|---|---|
| | 14 |
| | 15 |
| | 16 |
| | 17 |
| | 18 |
| | 19 |
| | 20 |
| | 21 |
| | 22 |
| | 23 |

TABLE 1-continued

| COMPOUND | EXAMPLE |
|---|---|
| (structure) | 25 |
| (structure) | 26 |
| (structure) | 27 |
| (structure) | 28 |
| (structure) | 29 |
| (structure) | 30 |
| (structure) | 31 |

TABLE 1-continued

| COMPOUND | EXAMPLE |
|---|---|
| (structure) | 37 |
| (structure) | 38 |
| (structure) | 39 |
| (structure) | 40 |
| (structure) | 41 |
| (structure) | 43 |
| (structure) | 44 |
| (structure) | 45 |
| (structure) | 46 |
| (structure) | 47 |

TABLE 1-continued

| COMPOUND | EXAMPLE |
|---|---|
| (structure) | 48 |
| (structure) | 49 |
| (structure) | 50 |
| (structure) | 52 |
| (structure) | 53 |
| (structure) | 55 |
| (structure) | 56 |
| (structure) | 57 |
| (structure) | 58 |

TABLE 1-continued

| COMPOUND | EXAMPLE |
|---|---|
| (structure) | 59 |
| (structure) | 60 |
| (structure) | 61 |
| (structure) | 62 |
| (structure) | 63 |
| (structure) | 64 |
| (structure) | 65 |
| (structure) | 66 |
| (structure) | 67 |

TABLE 1-continued

| COMPOUND | EXAMPLE |
|---|---|
| | 68 |
| | 69 |
| | 70 |
| | 71 |
| | 76 |
| | 77 |
| | 78 |
| | 79 |
| | 80 |
| | 81 |

TABLE 1-continued

| COMPOUND | EXAMPLE |
|---|---|
| 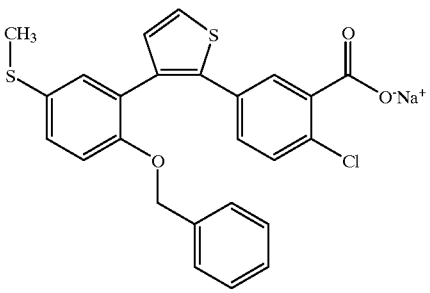 | 82 |
| 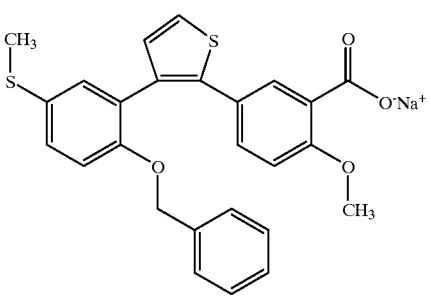 | 83 |
| 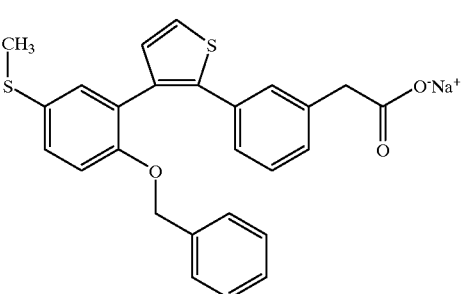 | 84 |
| 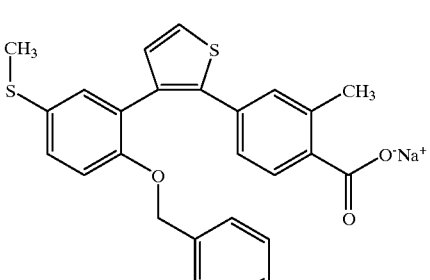 | 85 |

TABLE 1-continued

| COMPOUND | EXAMPLE |
|---|---|
| 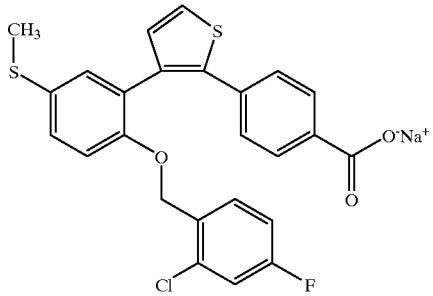 | 86 |
| 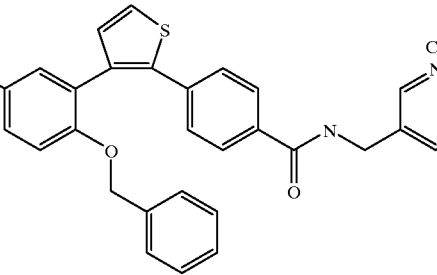 | 87 |
| 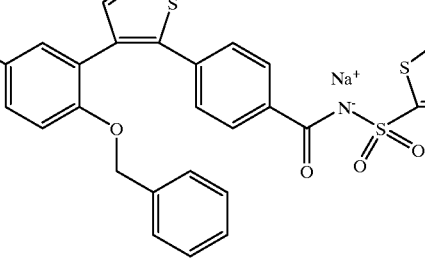 | 88 |

ASSAYS FOR DETERMINING BIOLOGICAL ACTIVITY

The compounds of formula A can be tested using the following assays to demonstrate their prostanoid antagonist or agonist activity in vitro and in vivo and their selectivity. The prostaglandin receptors investigated are DP, $EP_1$, $EP_2$, $EP_3$, $EP_4$, FP, IP and TP.

Stable Expression of Prostanoid Receptors in the Human Embryonic Kidney (HEK) 293(ebna) Cell Line Prostanoid receptor cDNAs corresponding to full length coding sequences were subcloned into the appropriate sites of mammalian expression vectors and transfected into HEK 293(ebna) cells. HEK 293(ebna) cells expressing the individual cDNAs were grown under selection and individual colonies were isolated after 2–3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 $\mu$M of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves for determination of ligand affinity.

Prostanoid Receptor Agonist and Antagonist Assays

Whole cell second messenger assays measuring stimulation ($EP_2$, $EP_4$, DP and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 $\mu$M RO-20174 (phosphodiesterase type IV inhibitor, available from Biomol) and, in the case of the $EP_3$ inhibition assay only, 15 $\mu$M forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both $K_B$ and slope values are calculated.

Rat Paw Edema Assay

The method is the same as described in Chan et al (J. Pharmacol. Exp. Ther. 274: 1531–1537, 1995).

LPS-Induced Pyrexia in Conscious Rats

The method is the same as described in Chan et al (J. Pharmacol. Exp. Ther. 274: 1531–1537, 1995).

LPS-Induced Pyrexia in Conscious Squirrel Monkeys

The method is the same as described in Chan et al (Eur. J. Pharmacol. 327: 221–225, 1997).

Acute Inflammatory Hyperalgesia Induced by Carrageenan in Rats

The method is the same as described in Boyce et al (Neuropharmacology 33: 1609–1611, 1994).

Adjuvant-Induced Arthritis in Rats

Female Lewis rats (body weight ~146–170 g) were weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of *Mycobacterium bittyricum* in 0.1 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day—1) and 21 days following adjuvant injection, and primary paw volumes were determined before (day—1) and on days 4 and 21 following adjuvant injection. The rats were anesthetized with an intramuscular injection of 0.03–0.1 mL of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0–4), narrowing or widening of joint spaces (0–5) subchondral erosion (0–3), periosteal reaction (0–4), osteolysis (0–4) subluxation (0–3), and degenerative joint changes (0–3). Specific criteria were used to establish the numerical grade of severity for each radiographic change. The maximum possible score per foot was 26. A test compound at total daily doses of 0.1, 0.3, 1, and 3 mg/kg/day, indomethacin at a total daily dose of 1 mg/kg/day, or vehicle (0.5% methocel in sterile water) are administered per os b.i.d. beginning post injection of adjuvant and continuing for 21 days. The compounds are prepared weekly, refrigerated in the dark until used, and vortex mixed immediately prior to administration.

EXAMPLES

The invention is illustrated in connection with the following non-limiting Examples. All the end products of the formula A were analyzed by NMR, TLC and mass spectrometry.

Intermediates were analyzed by NMR and TLC.

Most compounds were purified by flash chromatography on silica gel.

Recrystallization and/or swish (suspension in a solvent followed by filtration of the solid) with a solvent such as ether:hexane 1:1.

The course of reactions was followed by thin layer chromatography (TLC) and reaction times are given for illustration only.

Temperatures are in degrees Celsius.

Example 1

4-{3-[2-(phenylmethoxy)phenyl]-2-thienyl}benzoic Acid

2-Bromophenylbenzyl ether (3.5 g, 13.3 mmol, prepared from 2-bromophenol following standard benzylation procedure) was reacted with thiophene 3-boronic acid (2.1 g, 16.6 mmol, purchased from Lancaster), tetrakis (triphenylphosphine) palladium (770 mg, 0.7 mmol) and 2M $Na_2CO_3$ (25 mL) in 1,2-dimethoxyethane (75 mL) at 90° C. for 24 hours. The mixture was cooled down and a saturated solution of ammonium chloride and ethyl acetate were added. The separated aqueous layer was extracted with ethyl acetate (3×50 mL) and the combined organic layers were dried ($MgSO_4$ anh.), filtered and evaporated. Flash-chromatography of the residue (ethyl acetate-hexanes 1:10) yielded 3.5 g of thiophene 3 (Scheme 1) which was selectively brominated at the 2 position according to the following procedure: Thiophene 3 (2.4 g, 9.0 mmol) was treated with N-bromosuccinimide (1.6 g, 9.0 mmol) in THF (50 mL) containing 0.5 mL of water. The mixture was stirred at room temperature for 1.5 hours and water and diethyl ether were added. The separated aqueous layer was extracted with ether (3×50 mL) and the combined organic layers were dried ($MgSO_4$ anh.), filtered and evaporated. Flash-chromatography of the residue (ethyl acetate-hexanes 1:10) yielded 3.1 g of the bromothiophene 4. The 2-bromo thiophene derivative 4 (3.1 g, 9.0 mmol) was reacted with 4-carboxybenzeneboronic acid (1.5 g, 9.1 mmol), tetrakis (triphenylphosphine) palladium (520 mg, 0.5 mmol) and 2M $Na_2CO_3$ (14 mL) in 1,2-dimethoxyethane (100 mL) at 90° C. for 24 hours. The mixture was cooled down and a saturated solution of ammonium chloride and ethyl acetate were added. The separated aqueous layer was extracted with ethyl acetate (3×50 mL) and the combined organic layers were dried ($MgSO_4$ anh.), filtered and evaporated. Flash-chromatography of the residue (ethyl acetate-hexanes 1:10) yielded 1.9 g of the title compound. $^1$H nmr (400 MHz, $CD_3COCD_3$) δ ppm 7.87 (2H, d, J=11.5 Hz), 7.58 (1H, d, J=5.0 Hz), 7.35–7.09 (11H, m), 6.96 (1H, dt, J=10.0, 1.5 Hz), 4.95 (2H, s). Elemental analysis calculated for $C_{24}H_{17}SO_3Na.1.5H_2O$: C, 66.20, H, 4.63, S, 7.36; found: C, 66.00, H, 4.27, S, 7.44.

Example 2
4-{2-[2-(phenylmethoxy)phenyl]-3-thienyl}benzoic Acid

A mixture of 3-bromothiophene (725 mg, 7.7 mmol) (Scheme 2), carboethoxybenzeneboronic acid (1.1 g, 5.9 mmol), tetrakis(triphenylphosphine) palladium (444 mg, 0.4 mmol) and 2M $Na_2CO_3$ (9 mL) in 1,2-dimethoxyethane (60 mL) was heated at 90° C. for 24 hours. The mixture was cooled down and a saturated solution of ammonium chloride and ethyl acetate were added. The separated aqueous layer was extracted with ethyl acetate (3×50 mL) and the combined organic layers were dried ($MgSO_4$ anh.), filtered and evaporated. Flash-chromatography of the residue (ethyl acetate-hexanes 1:5) yielded 800 mg of thiophene derivative 9 which was converted to the bromide 10 using the conditions described above. The bromide 10 (1.3 g, 4.0 mmol) was treated with the boronic acid 11 (1.3 g, 6.0 mmol), tetrakis(triphenylphosphine) palladium (230 mg, 0.2 mmol) and 2M $Na_2CO_3$ (1.2 mL) in 1,2-dimethoxyethane (25 mL) at 90° C. for 24 hours. The mixture was cooled down and a saturated solution of ammonium chloride and ethyl acetate were added. The separated aqueous layer was extracted with ethyl acetate (3×50 mL) and the combined organic layers were dried ($MgSO_4$ anh.), filtered and evaporated. Flash-chromatography of the residue (ethyl acetate-hexanes 1:10) yielded 700 mg of the ester which was then heated at 50° C. for 5 hours in a (1:1) mixture of dioxane-water (10 mL total) in the presence of lithium hydroxide (210 mg). Work-up afforded 456 mg of the title compound. $^1$H nmr (400 MHz, $CD_3COCD_3$) δ ppm 8.11 (2H, d, J=11.5 Hz), 7.89 (2H, d, J=11.5 Hz), 7.63 (2H, d, J=11.5 Hz), 7.66 (1H, d, J=7.5 Hz), 7.59 (1H, d, J=7.5 Hz), 7.32, 7.22 (4H, 2m), 7.08 (2H, m), 6.97 (1H, dt, J=10.0, 1.5 Hz), 4.95 (2H, s). Elemental analysis calculated for $C_{24}H_{17}SO_3Na.1.5H_2O$: C, 66.20, H, 4.63, S, 7.36; found:

Example 3
2-(4-{3-[2-(phenylmethoxy)phenyl]-2-thienyl}phenyl) acetic Acid

Prepared following the standard procedure described in example 1. $^1$H nmr (400 MHz, $CD_3COCD_3$) δ ppm 7.47 (1H, d, J=7.5 Hz), 7.30–7.06 (14H, m), 6.91 (1H, t, J=7.5 Hz), 4.95 (2H, s), 3.60 (2H, s).

Example 4
(4-{3-[2-(phenylmethoxy)phenyl]-2-thienyl}phenyl) methan-1-ol

To a solution of ethyl ester of example 1 (39 mg, 0.096 mmol) in THF (1.5 mL) at −78° C. was added $Et_3BHLi$ (1M in THF, 0.38 mL, 0.38 mmol) and the reaction was warmed to room temperature and stirred for 1 h. The mixture was quenched with saturated $NH_4Cl$, diluted with $Et_2O$ and washed successively with HCl 10%, aq. $NaHCO_3$ and brine. The ether layer was dried with anh. $MgSO_4$, filtered and concentrated under reduced pressure to give a residue which was purified by flash chromatography (75% Hexanes/25% AcOEt) to provide the title compound (28.3 mg). $^1$H nmr (400 MHz, acetone-$d_6$) δ ppm 7.45 (1H, d, J=7.5 Hz), 7.32–7.05 (13H, m), 6.91 (1H, t, J=7.5 Hz), 4.97 (2H, s), 4.60 (2H, d, J=7.5 Hz), 3.95 (1H, t, J=7.5 Hz).

Example 5
2-(4-{3-[2-(phenylmethoxy)phenyl]-2-thienyl}phenyl) propan-2-ol

To a solution of ethyl ester of example 1 (34 mg, 0.084 mmol) in ether (1.5 mL) at −78° C. was added MeMgBr (3M in ether, 0.11 mL, 0.33 mmol) and the reaction was warmed to room temperature and stirred for 1 h. The mixture was quenched with saturated $NH_4Cl$, diluted with $Et_2O$ and washed successively with HCl 10%, aq. $NaHCO_3$ and brine. The ether layer was dried with anh. $MgSO_4$, filtered and concentrated under reduced pressure to give a residue which was purified by flash chromatography (75% Hexanes/25% AcOEt) to provide the title compound (25.6 mg). $^1$H nmr (400 MHz, acetone-$d_6$) δ ppm 7.45–7.35 (3H, m), 7.39–7.05 (11H, m), 6.91 (1H, t, J=7.5 Hz), 4.95 (2H, s), 3.95 (1H, bs), 1.47 (6H, s).

Example 6
1-(4-{3-[2-(phenylmethoxy)phenyl]-2-thienyl}phenyl) ethan-1-ol

To a solution of the alcohol of example 4 (200 mg, 0.536 mmol) in $CH_2Cl_2$ is added $MnO_2$ (467 mg, 5.36 mmol) and the mixture is stirred overnight. The reaction is then filtered throught a plug of celite and the crude mixture diluted in ether (5.0 mL) and cooled at −78° C. MeMgBr was then added (3M in ether, 0.22 mL, 0.66 mmol) and the reaction was warmed to room temperature and stirred for 1 h. The mixture was quenched with saturated $NH_4Cl$, diluted with $Et_2O$ and washed successively with HCl 10%, aq. $NaHCO_3$ and brine. The ether layer was dried with anh. $MgSO_4$, filtered and concentrated under reduced pressure to give a residue which was separated in two and one part was purified by flash chromatography (70% Hexanes/30% AcOEt) to provide the title compound (19.4 mg). $^1$H nmr (400 MHz, acetone-$d_6$) δ ppm 7.45 (1H, d, J=7.5 Hz), 7.32–7.05 (13H, m), 6.91 (1H, t, J=7.5 Hz), 4.97 (2H, s), 4.80 (1H, m) 4.12 (1H, d, J=5.0 Hz), 3.95 (3H, d, J=7.5 Hz).

Example 7
4-{5-bromo-3-[2-(phenylmethoxy)phenyl]-2-thienyl}benzoic Acid

To a solution of example 1 (0.48 g, 1.2 mmol) in THF/water (10/0.1 mL) was added N-bromosuccinimide (0.22 g, 1.2 mmol). The reaction was stirred overnight at room temperature. The mixture was then diluted with AcOEt and water, and the combined organic layer was washed with HCl 10%, $NaHCO_3$ (aq), brine, drier (anh. $MgSO_4$) and concentrated under reduced pressure to give a residue which was purified by flash chromatography (95% CH$_2$Cl$_2$/5% AcOEt) and crystalisation (CH$_2$Cl$_2$/Hexanes) to provide the title compound (0.16 g). $^1$H nmr (400 MHz, acetone-d$_6$) d ppm 7.76 (2H, d, J=8.38 Hz), 7.23–7.11 (7H, m), 6.95 (2H, m), 6.87 (2H, d, J=8.16 Hz), 6.71 (1H, t, J=7.5 Hz), 4.90 (2H, s). Elemental analysis calculated for C$_{24}$H$_{16}$BrNaSO$_3$.4 H$_2$O: C, 51.53; H, 4.32, S, 5.73: found: C, 51.14; H, 4.32, S, 5.73: found: C, 51.14; H, 3.76, S, 5.52.

Example 8
4-{3-[5-chloro-2-(phenylmethoxy)phenyl]-2-theinyl}benzoic Acid

Prepared following the procedure described in example 1. $^1$H nmr (400 MHz, CD$_3$COCD$_3$) δ ppm 7.90 (2H, d, J=11.5 Hz), 7.58 (1H, d, J=5.0 Hz), 7.38–7.05 (11H, m), 4.94 (2H, s). Elemental analysis calculated for C$_{24}$H$_{16}$ClSO$_3$Na.H$_2$O: C, 62.54; H, 3.94, S, 6.96; found: C, 62.14; H, 3.82; S, 6.38.

Example 9
3-{3-[5-chloro-2-(phenylmethoxy)phenyl]-2-thienyl}benzoic Acid

Prepared following the procedure described in example 1. $^1$H nmr (400 MHz, CD$_3$COCD$_3$) δ ppm 7.56–7.10 (14H, m), 5.13 (2H, s).

Example 10
2-chloro-5-{3-[5-chloro-2-(phenylmethoxy)phenyl](2-thienyl)}benzoic Acid Prepared following the procedure described in example 1. $^1$H nmr (400 MHz, acetone-d$_6$) δ ppm 7.80 (1H, d, J=2.2 Hz), 7.57 (1H, d, J=5.22 Hz), 7.40–7.20 (8H, m), 7.12–7.07 (3H, m), 4.92 (2H, s). Elemental analysis calculated for C$_{24}$H$_{15}$Cl$_2$NaSO$_3$.4 H$_2$O: C, 52.46; H, 4.22, S, 5.84; found: C, 52.05; H, 3.95, S, 5.54.

Example 11
2-[2-(3-(2H-1,2,3,4-tetraazol-5-yl)phenyl)(3-thienyl)]-4-chloro-1-(phenylmethoxy)benzene To a solution of nitrile corresponding to the acid of example 9 (0.10 g, 0.26 mmol) in N-methyl pyrrolidine was added pyridine hydrochloride (0.30 g, 2.6 mmol) and sodium azide (0.34 g, 5.2 mmol). The reaction was stirred for 36 h. at 135° C., cooled down and then quenched by adding HCl 10%, diluted with AcOEt, washed with HCl 10%, brine, dried (anh. MgSO$_4$) and concentrated under reduced pressure to give a residue which was purified by flash-chromatography (80% CH$_2$Cl$_2$/19% AcOEt/1% AcOH), then crystalised (CH$_2$Cl$_2$/Hexanes to provide the title compound (0.05 g). $^1$H nmr (400 MHz, acetone-d$_6$) δ ppm 8.10 (1H, s), 8.01 (1H, d, J=7.5 Hz), 7.57 (1H, d, J=5.22 Hz), 7.45 (1H, t, J=7.5 Hz), 7.33 (1H, d, J=7.5 Hz), 7.30 (1H, d, J=7.5 Hz), 7.25–7.12 (5H, m), 7.07 (3H, m), 4.92 (2H, s).

Example 12
5-{3-[5-chloro-2-(phenylmethoxy)phenyl](2-thienyl)}-2-methoxybenzoic Acid Prepared following the procedure described in example 1. $^1$H nmr (400 MHz, acetone-d$_6$) δ ppm 7.87 (1H, d, J=2.30 Hz), 7.48 (1H, d, J=5.22 Hz), 7.37 (1H, dd, J=8.80, 2.70 Hz), 7.32–7.20 (4H, m), 7.18–7.05 (6H, m), 4.97 (2H, s), 3.95 (3H, s). Elemental analysis calculated for C$_{25}$H$_{18}$ClNaSO$_4$.3H$_2$O: C, 56.98; H, 4.59, S, 6.08: found: C, 56.86; H, 3.95, S, 5.50.

Example 13
3-{3-[5-chloro-2-(phenylmethoxy)phenyl](2-thienyl)}-4-fluorobenzoic Acid Prepared following the procedure described in example 1. $^1$H nmr (400 MHz, acetone-d$_6$) δ ppm 8.00 (2H, m), 7.65 (1H, d, J=5.20 Hz), 7.30–7.10 (9H, m), 7.03 (1H, d, J=8.0 Hz), 4.95 (2H, s), 1.97 (3H, s). Elemental analysis calculated for C$_{24}$H$_{15}$ClFNaSO$_3$.2 H$_2$O: C, 58.01; H, 3.85: found: C, 58.01; H, 3.40.

Example 14
3-{3-[5-chloro-2-(phenylmethoxy)phenyl]-2-thienyl}benzamide

To a solution of the acid of example 9 (0.45 g, 1.1 mmol) in pyridine (10 mL) at 0° C. was added methanesulfonyl chloride (0.10 mL, 1.3 mmol) and the reaction was stirred for 1 h. at 0° C. Ammonia was then introduced and the mixture was stirred for 1 h. at room temperature. The mixture was slowly quenched by adding HCl 10%, diluted with AcOEt, washed with HCl 10%, NaHCO$_3$ (aq), brine, dried (anh. MgSO$_4$) and concentrated under reduced pressure to give a residue which was purified by crystalisation (AcOEt/Hexanes) to provide the title compound (0.4 g). $^1$H nmr (400 MHz, acetone-d$_6$) δ ppm 7.92 (1H, s), 7.81 (1H, d, J=3.57 Hz), 7.54 (1H, d, J=5.17 Hz), 7.38 (1H, bs), 7.31–7.23 (6H, m), 7.18 (1H, d, J=5.10 Hz) 7.15–7.02 (4H, m), 6.62 (1H,bs), 4.95 (2H, s). Elemental analysis calculated for C$_{24}$H$_{18}$ClNSO$_2$.H$_2$O: C, 65.82; H, 4.60; N, 3.20; S, 7.32; found: C, 66.21; H, 4.23; N, 3.00; S, 7.53.

Example 15
2-(3-{3-[5-chloro-2-(phenylmethoxy)phenyl]-2-thienyl}phenyl)acetic Acid Prepared following the procedure described in example 1. $^1$H nmr (400 MHz, acetone-d$_6$) δ ppm 7.49 (1H, d, J=5.2 Hz), 7.29–7.05 (13H, m), 4.91 (2H, s), 3.52 (2H, s). Elemental analysis calculated for C$_{25}$H$_{18}$ClNaSO$_3$.1.5 H$_2$O: C, 62.04; H, 4.37, S, 6.62: found: C, 61.63; H, 4.14, S, 6.37.

Example 16
4-{3-[5-chloro-2-(phenylmethoxy)phenyl](2-thienyl)}-2-methylbenzoic Acid Prepared following the procedure described in example 1. $^1$H nmr (400 MHz, CD$_3$COCD$_3$) δ ppm 7.80 (1H, d, J=10.5 Hz), 7.50 (1H, d, J=7.0 Hz), 7.28–7.00 (11H, m), 4.88 (2H, s), 2.05 (3H, s). Elemental analysis calculated for C$_{25}$H$_{18}$ClSO$_3$Na.1.5H$_2$O: C, 62.05, H, 4.37, S, 6.63; found: C, 62.34, H, 4.00, S, 6.16.

Example 17
4-(3-{2-[(2-chloro-4-fluorophenyl)methoxy]-5-nitrophenyl}-2-thienyl)benzoic Acid Prepared following the procedure described in example 1. $^1$H nmr (400 MHz, acetone-d$_6$) δ ppm 8.28 (1H, dd, J=9.13, 2.88 Hz), 8.10 (1H, d, J=2.87 Hz), 7.87 (2H, d, J=8.52 Hz), 7.64 (1H, d, J=5.20 Hz), 7.39–7.14 (6H, m), 7.05 (1H, dt, J=8.44, 2.60 Hz), 5.14 (2H, s). Elemental analysis calculated for C$_{24}$H$_{14}$FClNNaSO$_5$.2 H$_2$O: C, 53.19; H, 3.34; N, 2.58; S, 5.92: found: C, 52.71; H, 2.90; N, 2.52; S, 5.67.

Example 18
(4-{3-[5-chloro-2-(phenylmethoxy)phenyl](2-thienyl)}phenyl)-N-(3-pyridylmethyl)formamide The benzoic acid of example 8 (900 mg, 2.2 mmol) was added at −78° C. to a mixture of EDCI (820 mg, 4.4 mmol) and 3-aminomethylpyridine (330 μL, 3.0 mmol) in dichloromethane (20 mL). The mixture was warmed to room temperature and stirred for 12 hours, and a 10% solution of sodium bicarbonate was added. The separated aqueous layer was extracted with dichloromethane (3×50 mL) and the combined organic layers were dried (MgSO$_4$ anh.), filtered and evaporated. Flash-chromatography of the residue (ethyl acetate:dichloromethane, 3:7) yielded 450 mg of the title compound. ¹H nmr (400 MHz, CD₃COCD₃) δ ppm 8.60 (1H, br. s.), 8.46 (1H, m), 8.31 (1H, m), 7.82 (2H, d, J=11.5 Hz), 7.77 (1H, d, J=11.5 Hz), 7.56 (1H, d, J=7.5 Hz), 7.31–7.16 (9H, m), 7.06 (3H, m), 4.94 (2H, s), 4.62 (2H, br. d). Elemental analysis calculated for $C_{30}H_{24}ClN_2SO_2Na·H_2O$: C, H, S; found: C, H, S.

Example 19
[4-(3-{2-[(2-chloro-4-fluorophenyl)methoxy]-5-nitrophenyl}(2-thienyl))phenyl]-N-(3-pyridylmethyl) formamide Prepared following the procedure described for example 18. ¹H nmr (400 MHz, acetone-d₆) δ ppm 8.78 (1H, s), 8.68 (1H, bs), 8.63 (1H, d, J=3.8 Hz), 8.35 (1H, d, J=8.16 Hz), 8.27 (1H, dd, J=9.13, 2.90 Hz), 8.08 (1H, d, J=2.86 Hz), 7.79 (3H, m), 7.62 (1H, d, J=5.20 Hz), 7.37 (1H, d, J=9.13 Hz), 7.27 (5H, m), 7.08 (1H, m), 5.13 (2H, s), 4.75 (2H, d, J=5.71 Hz).

Example 20
(4-{3-[5-chloro-2-(phenylmethoxy)phenyl](2-thienyl)}phenyl)-N-(2-thienylsulfonyl)formamide The benzoic acid of example 8 (350 mg, 0.8 mmol) was added at room temperature to a mixture of EDCI (175 mg, 0.9 mmol), 4-dimethylaminopyridine (300 mg, 2.5 mmol) and 2-sulfonamidothiophene (156 mg, 1.0 mmol) in dichloromethane (12 mL). The mixture was stirred for 12 hours at room temperature and a 1N solution of HCl was added. The separated aqueous layer was extracted with dichloromethane (3×50 mL) and the combined organic layers were dried ($MgSO_4$ anh.), filtered and evaporated. Flash-chromatography of the residue (ethyl acetate:dichloromethane, 3:7) was followed by trituration in dichloromethane:hexanes (1:10) yielded 290 mg of the title compound. ¹H nmr (400 MHz, CD₃COCD₃) δ ppm 7.99 (1H, dd, J=5.5, 1.5 Hz), 7.91 (1H, m), 7.81 (2H, d, J=11.5 Hz), 7.60 (1H, d, J=7.5 Hz), 7.31 (2H, d, J=10.0 Hz), 7.29 (1H, m), 7.20 (6H, m), 7.10 (1H, d, J=11.5 Hz), 7.06 (2H, m), 4.91 (2H, s). Elemental analysis calculated for $C_{28}H_{19}ClNS_3O_4Na·1.5H_2O$: C, 54.67, H, 3.61, S, 15.64, N, 2.28; found: C, 54.28, H, 3.24, S, 15.60, N, 2.29.

Example 21
4-(3-{2-[(2,4-difluorophenyl)methoxy]-5-chlorophenyl}(2-thienyl))-3-methylbenzoic Acid Prepared following the procedure described in example 1. ¹H nmr (400 MHz, acetone-d₆) δ ppm 7.77 (2H, m), 7.50 (2H, m), 7.29–7.17 (4H, m), 7.07 (2H, m), 6.93 (1H, d, J=2.3 Hz), 5.09 (2H, s), 1.97 (3H, s). Elemental analysis calculated for $C_{25}H_{16}ClF_2NaSO_3·2.5H_2O$: C, 55.82; H, 3.93; S, 5.96: found: C, 55.61; H, 3.41; S, 5.87.

Example 22
4-(3-{5-chloro-2-[(4-fluorophenyl)methoxy]phenyl}(2-thienyl))-3-methylbenzoic Acid Prepared following the procedure described in example 1. ¹H nmr (400 MHz, acetone-d₆) δ ppm 7.80 (2H, m), 7.60 (1H, d, J=5.2 Hz), 7.35–7.25 (4H, m), 7.20 (1H, dd, J=7.5, 2.2 Hz), 7.12–7.02 (3H, m), 6.98 (1H, d, J=2.2 Hz), 5.03 (2H, s), 2.05 (3H, s). Elemental analysis calculated for $C_{25}H_{17}ClFNaSO_3·1.5H_2O$: C, 59.82; H, 4.01: found: C, 59.74; H, 3.67.

Example 23
4-{3-[5-chloro-2-(phenylmethoxy)phenyl](2-thienyl)}-3-methylbenzoic Acid Prepared following the procedure described in example 1. ¹H nmr (400 MHz, acetone-d₆) δ ppm 7.80 (2H, m), 7.58 (1H, d, J=5.2 Hz), 7.35–7.15 (8H, m), 7.04–6.98 (2H, m), 5.03 (2H, s), 2.05 (3H, s). Elemental analysis calculated for $C_{25}H_{18}ClNaSO_3·1 H_2O$: C, 63.22; H, 4.24; S, 6.75: found: C, 63.11; H, 4.04; S, 6.62.

Example 24
4-{4-[2-(phenylmethoxy)phenyl]-3-thienyl}benzoic Acid 3,4-bromothiophene (920 μL, 7.7 mmol) was treated with 8 (500 mg, 2.6 mmol), tetrakis(triphenylphosphine) palladium (150 mg, 0.15 mmol) and 2M $Na_2CO_3$ in 1,2-dimethoxyethane (25 mL) at 90° C. for 12 hours. The mixture was cooled and a saturated solution of ammonium chloride and ethyl acetate were added. The separated aqueous layer was extracted with ethyl acetate (3×50 mL) and the combined organic layers were dried ($MgSO_4$ anh.), filtered and evaporated. Flash-chromatography of the residue (ethyl acetate: hexanes, 1:8) yielded 420 mg of 15 which was then treated with boronic acid 11 following a procedure similar to those already described (vide supra) to provide 16. Ethyl ester 16 (560 mg, 1.4 mmol) was then hydrolyzed with 1N lithium hydroxide (8 mL) in dioxane (16 mL) at 50° C. for 5 hours. The mixture was cooled down and a 1N solution of HCl and ethyl acetate were added. The separated aqueous layer was extracted with ethyl acetate (3×50 mL) and the combined organic layers were dried ($MgSO_4$ anh.), filtered and evaporated. Flash-chromatography of the residue (dichloromethane:ethyl acetate:acetic acid, 95:4:1) provided the title compound. ¹H nmr (400 MHz, acetone-d₆) δ ppm 7.84 (2H, d, J=8.1 Hz), 7.63 (1H, d, J=3.2 Hz), 7.46 (1H, d, J=3.1 Hz), 7.29–7.20 (7H, m), 6.99–6.93 (4H, m), 4.76 (2H, s). Elemental analysis calculated for $C_{30}H_{25}N_2SClO_2·1 H_2O$: C, 67.59; H, 4.49: found: C, 67.54; H, 4.33.

Example 25
(4-{4-[2-(phenylmethoxy)phenyl](3-thienyl)}phenyl)-N-(3-pyridylmethyl)formamide Prepared following the standard procedure described for example 18 ¹H nmr (400 MHz, CD₃COCD₃) δ ppm 8.60 (1H, d, J=1.7 Hz), 8.45 (1H, dd, J=4.8, 1.6 Hz), 8.30 (1H, bs), 7.75 (3H, m), 7.60 (1H, d, J=3.3 Hz), 7.45 (1H, d, J=3.3 Hz), 7.23 (8H, m), 6.95 (4H, m), 4.77 (2H, s), 4.60 (2H, d, J=6.1 Hz). Elemental analysis calculated for $C_{30}H_{25}N_2SClO_2·0.5 H_2O$: C, 69.02; H, 5.02; N, 5.37; S, 6.15: found: C, 68.51; H, 5.06; N, 5.39; S, 6.62.

Example 26
4-[3-(2-{[4-(difluoromethoxy)phenyl]methoxy}-5-chlorophenyl)(2-thienyl)]-3-methylbenzoic Acid Prepared following the standard procedure described in example 1 ¹H nmr (400 MHz, CD₃COCD₃) δ ppm 7.82 (1H, s), 7.80 (1H, d, J=11.5 Hz), 7.60 (1H, d, J=7.5 Hz), 7.32 (4H, m), 7.20 (1H, dd, J=11.5, 1.5 Hz), 7.18 (2H, m), 7.09 (1H, d, J=11.5 Hz), 6.97 (1H, s), 5.06 (2H, s).

Example 27
4-(3-{2-[(4-carboxyphenyl)methoxy]-5-chlorophenyl}-2-thienyl)benzoic Acid Prepared following the standard procedure described in example 1 ¹H nmr (400 MHz, CD₃COCD₃) δ ppm 7.88 (4H, t. J=7.0 Hz), 7.62 (1H, d, J=6.0 Hz), 7.31 (3H, m), 7.19 (4H, m), 7.10 (1H, d, J=11.5 Hz), 5.04 (2H, s). Elemental analysis calculated for $C_{25}H_{15}ClN_2SO_5Na·6H_2O$: C, 48.67, H, 4.41; found: C, 49.00, H, 3.50.

Example 28
3-(3-{2-[(4-carboxyphenyl)methoxy]-5-chlorophenyl}-2-thienyl)benzoic Acid Prepared following the standard procedure described in example 1 ¹H nmr (400 MHz, CD₃COCD₃) δ ppm 7.98 (1H, s.), 7.92 (3H, m), 7.59 (1H, d, J=7.5 Hz), 7.45 (1H, m), 7.40 (1H, t, J=10.0 Hz), 7.33 (1H, dd, J=11.5. 1.5 Hz), 7.21 (4H, m), 7.09 (1H, d, J=11.5 Hz), 5.01 (2H, s).

Example 29
4-(3-{5-chloro-2-[(2-chloro-4-fluorophenyl)methoxy]phenyl}(2-thienyl))-3-methylbenzoic Acid Prepared following the standard procedure described in example 1 $^1$H nmr (400 MHz, CD$_3$COCD$_3$) δ ppm 7.79 (2H, m), 7.59 (1H, d, J=5.2 Hz), 7.36–7.05 (7H, m), 7.00 (1H, d, J=2.68 Hz), 5.07 (2H, s), 2.04 (3H, s). Elemental analysis calculated for C$_{25}$H$_{16}$Cl$_2$FNaSO$_3$·H$_2$O: C, 56.94; H, 3.44; S, 6.08: found: C, 57.18; H, 3.40; S, 6.33.

Example 30
[4-(3-{5-chloro-2-[(2-chloro-4-fluorophenyl)methoxy]phenyl}(2-thienyl))-3-methylphenyl]-N-(3-pyridylmethyl)formamide Prepared following the standard procedure described for example 18 $^1$H nmr (400 MHz, acetone-d$_6$) δ ppm 8.61 (1H, s), 8.42 (2H, m), 7.80–7.65 (3H, m), 7.53 (1H, d, J=5.18 Hz), 7.45–7.00 (9H, m), 5.05 (2H, s), 4.60 (2H, d, J=7.5 Hz), 2.00 (3H, s). Elemental analysis calculated for C$_{31}$H$_{24}$N$_2$Cl$_3$SFO$_2$·0.5H$_2$O: C, 59.77; H, 4.05; N, 4.50; S, 5.15: found: C, 59.91; H, 4.22; N, 4.47; S, 5.38.

What is claimed is:

1. A compound represented by formula A

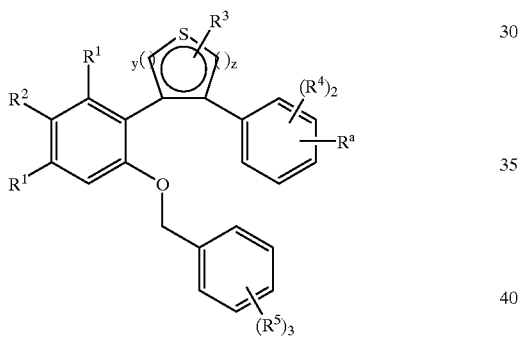

A or a pharmaceutically acceptable salt, hydrate or ester thereof, wherein:
  y and z are independently 0–2, with the proviso that y+z=2;
  $R^a$ is selected from the group consisting of:
    1) heteroaryl, wherein heteroaryl is selected from the group consisting of:
      a) furyl,
      b) diazinyl, triazinyl or tetrazinyl,
      c) imidazolyl,
      d) isoxazolyl,
      e) isothiazolyl,
      f) oxadiazolyl,
      g) oxazolyl,
      h) pyrazolyl,
      i) pyrrolyl,
      j) thiadiazolyl,
      k) thiazoyl
      l) thienyl
      m) triazolyl and
      n) tetrazolyl, wherein heteroaryl is optionally substituted with one or more substituents independently selected from $R^{11}$ or $C_{1-4}$alkyl,
    2) —COR$^6$,
    3) —NR$^7$R$^8$,
    4) —SO$_2$R$^9$,
    5) hydroxy,
    6) C$_{1-6}$alkoxy, optionally substituted with one or more substituents independently selected from $R^{11}$, and
    7) C$_{1-6}$alkyl, C$_{2-6}$alkenyl or C$_{3-6}$cycloalkyl, optionally substituted with one or more substituents independently selected from $R^{11}$, and further substituted with 1–3 substituents independently selected from the group consisting of:
      (a) —COR$^6$
      (b) —NR$^7$R$^8$,
      (c) —SO$_2$R$^9$,
      (d) hydroxy,
      (e) C$_{1-6}$alkoxy or haloC$_{1-6}$alkoxy, and
      (f) heteroaryl,
  with the proviso that $R^a$ is positioned on the phenyl ring to which it is bonded in a 1,3 or 1,4 relationship relative to the thienyl group represented in formula A;
  each $R^1$, $R^2$, $R^3$, $R^4$ and $R^5$ are independently selected from the group consisting of:
    1) hydrogen,
    2) halogen,
    3) C$_{1-6}$alkyl,
    4) C$_{1-6}$alkoxy,
    5) C$_{1-6}$alkylthio,
    6) nitro,
    7) carboxy and
    8) CN, wherein items (3)–(5) above are optionally substituted with one or more substituents independently selected from $R^{11}$;
  $R^6$ is selected from the group consisting of hydrogen, hydroxy, C$_{1-6}$alkyl, C$_{1-6}$alkoxy and NR$^7$R$^8$, wherein C$_{1-6}$alkyl or C$_{1-6}$alkoxy are optionally substituted with one or more substituents independently selected from $R^{11}$;
  $R^7$ and $R^8$ are independently selected from the group consisting of:
    (1) hydrogen,
    (2) hydroxy,
    (3) SO$_2$R$^9$
    (4) C$_{1-6}$alkyl,
    (5) C$_{1-6}$alkoxy,
    (6) phenyl,
    (7) naphthyl,
    (8) furyl,
    (9) thienyl and
    (10) pyridyl, wherein items (4)–(5) above are optionally substituted with one or more substituents independently selected from $R^{11}$, and items (6)–(10) above are optionally substituted with one or more substituents independently selected from $R^{11}$ or C$_{1-4}$alkyl,
  $R^9$ is selected from the group consisting of
    (1) hydroxy,
    (2) N(R$^{10}$)$_2$,
    (3) C$_{1-6}$alkyl, optionally substituted with one or more substituents independently selected from $R^{11}$,
    (4) phenyl,
    (5) naphthyl,
    (6) furyl,
    (7) thienyl and
    (8) pyridyl, wherein items (4)–(8) above are optionally substituted with one or more substituents independently selected from $R^{11}$ or C$_{1-4}$alkyl;
  $R^{10}$ is hydrogen or C$_{1-6}$alkyl; and $R^{11}$ is the group consisting of halogen, hydroxy, $C_{1-3}$alkoxy, nitro, $N(R^{10})_2$ and pyridyl.

2. A compound in accordance with claim 1 wherein: $R^a$ is selected from the group consisting of: heteroaryl, as originally defined, $COR^6$, wherein $R^6$ is as originally defined, $C_{1-6}$ alkyl and $C_{2-6}$ alkenyl, optionally substituted as originally defined, and $SO_2R^9$ with $R^9$ as originally defined.

3. A compound in accordance with claim 2 wherein $R^a$ is selected from the group consisting of:

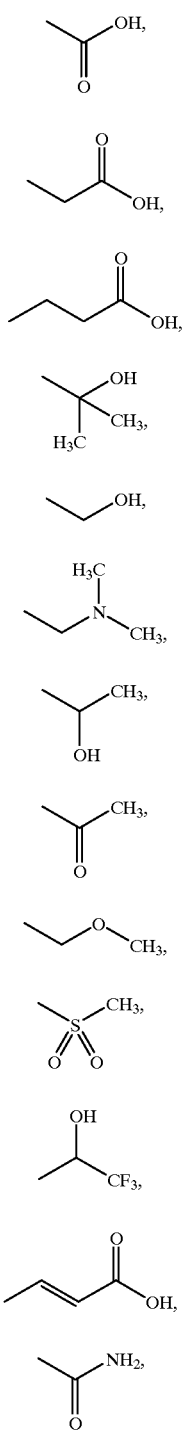

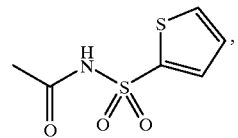

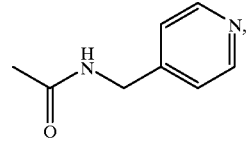

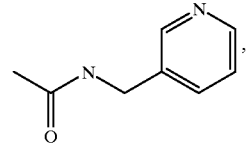

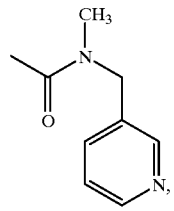

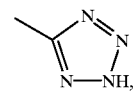

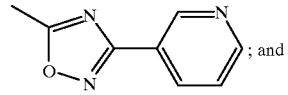

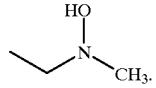

4. A compound in accordance with claim 1 wherein 1–3 of $R^1$ and $R^2$ are selected from the group consisting of halo, $C_{1-4}$ alkyl, $C_{1-4}$ alkoxy, $C_{1-4}$ alkylthio and $NO_2$.

5. A compound in accordance with claim 1 wherein each $R^4$ and $R^5$ independently represents a member selected from the group consisting of: H, halo, $C_{1-6}$ alkyl and $C_{1-6}$ alkoxy, said alkyl and alkoxy groups being optionally substituted as originally defined.

6. A compound in accordance with claim 1 wherein each $R^3$ independently represents a member selected from the group consisting of: H and halo.

7. A compound in accordance with claim 1 wherein one of y and z represents 0 and the other represents 2.

8. A compound in accordance with claim 1 wherein:
$R^a$ is selected from the group consisting of: heteroaryl, as originally defined, $COR^6$, wherein $R^6$ is as originally defined, $C_{1-6}$ alkyl and $C_{2-6}$ alkenyl, optionally substituted as originally defined, and $SO_2R^9$ with $R^9$ as originally defined;
1–3 of $R^1$ and $R^2$ are selected from the group consisting of halo, $C_{1-4}$ alkyl, $C_{1-4}$ alkoxy, $C_{1-4}$ alkylthio and $NO_2$;
each $R^4$ and $R^5$ independently represents a member selected from the group consisting of: H, halo, $C_{1-6}$ alkyl and $C_{1-6}$ alkoxy, said alkyl and alkoxy groups being optionally substituted as originally defined;

each $R^3$ independently represents a member selected from the group consisting of: H and halo;

and one of y and z represents 0 and the other represents 2.

9. A compound in accordance with claim 1 wherein:

$R^a$ is selected from the group consisting of:

(1) 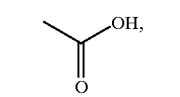

(2) 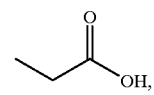

(3) 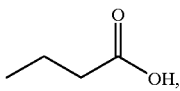

(4) 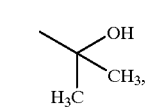

(5) 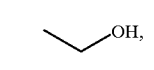

(6) 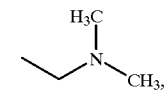

(7) 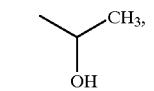

(8) 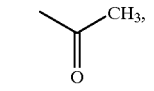

(9) 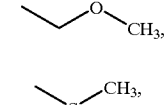

(10) 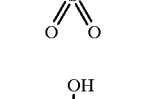

(11) 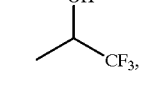

(12) 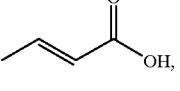

(13) 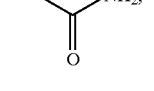

(14) 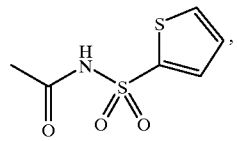

(15) 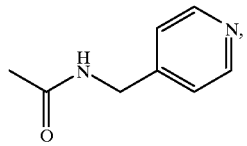

(16) 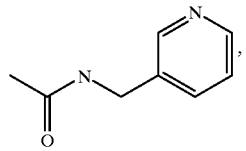

(17) 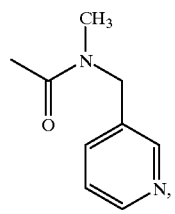

(18) 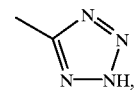

(19) 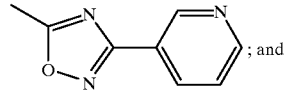

; and

(20) 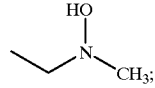

1–3 of $R^1$ and $R^2$ are selected from the group consisting of halo, $C_{1-4}$ alkyl, $C_{1-4}$ alkoxy, $C_{1-4}$ alkylthio and $NO_2$;

each $R^4$ and $R^5$ independently represents a member selected from the group consisting of: H, halo, $C_{1-6}$ alkyl and $C_{1-6}$ alkoxy, said alkyl and alkoxy groups being optionally substituted as originally defined;

each $R^3$ independently represents a member selected from the group consisting of: H and halo;

and one of y and z represents 0 and the other represents 2.

10. A compound selected from the group consisting of:
(a) 4-{3-[2-(Phenylmethoxy)phenyl]-2-thienyl}benzoic acid;
(b) 4-{2-[2-(Phenylmethoxy)phenyl]-3-thienyl}benzoic acid;
(c) 2-(4-{3-[2-(phenylmethoxy)phenyl]-2-thienyl}phenyl) acetic acid;
(d) (4-{3-[2-(phenylmethoxy)phenyl]-2-thienyl}phenyl) methan-1-ol;
(e) 2-(4-{3-[2-(phenylmethoxy)phenyl]-2-thienyl}phenyl) propan-2-ol;
(f) 1-(4-{3-[2-(phenylmethoxy)phenyl]-2-thienyl}phenyl) ethan-1-ol;

(g) 4-{5-bromo-3-[2-(phenylmethoxy)but-2-enyl]-2-thienyl}benzoic acid;
(h) 4-{3-[5-chloro-2-(phenylmethoxy)phenyl]-2-thienyl}benzoic acid;
(i) 3-{3-[5-chloro-2-(phenylmethoxy)phenyl]-2-thienyl}benzoic acid;
(j) 2-chloro-5-{3-[5-chloro-2-(phenylmethoxy)phenyl](2-thienyl)}benzoic acid;
(k) 2-[2-(3-(2H-1,2,3,4-tetraazol-5-yl)phenyl)(3-thienyl)]-4-chloro-1-(phenylmethoxy)benzene;
(l) 5-{3-[5-chloro-2-(phenylmethoxy)phenyl](2-thienyl)}-2-methoxybenzoic acid;
(m) 3-{3-[5-chloro-2-(phenylmethoxy)phenyl](2-thienyl)}-4-fluorobenzoic acid;
(o) 3-{3-[5-chloro-2-(phenylmethoxy)phenyl]-2-thienyl}benzamide;
(p) 2-(3-{3-[5-chloro-2-(phenylmethoxy)phenyl]-2-thienyl}phenyl)acetic acid;
(q) 4-{3-[5-chloro-2-(phenylmethoxy)phenyl](2-thienyl)}-2-methylbenzoic acid;
(r) 4-(3-{2-[(2-chloro-4-fluorophenyl)methoxy]-5-nitrophenyl}-2-thienyl)benzoic acid;
(s) (4-{3-[5-chloro-2-(phenylmethoxy)phenyl](2-thienyl)}phenyl)-N-(3-pyridylmethyl)formamide;
(t) [4-(3-{2-[(2-chloro-4-fluorophenyl)methoxy]-5-nitrophenyl}(2-thienyl))phenyl]-N-(3-pyridylmethyl)formamide;
(u) (4-{3-[5-chloro-2-(phenylmethoxy)phenyl](2-thienyl)}phenyl)-N-(2-thienylsulfonyl)formamide;
(v) 4-(3-{2-[(2,4-difluorophenyl)methoxy]-5-chlorophenyl}(2-thienyl))-3-methylbenzoic acid;
(w) 4-(3-{5-chloro-2-[(4-fluorophenyl)methoxy]phenyl}(2-thienyl))-3-methylbenzoic acid;
(x) 4-{3-[5-chloro-2-(phenylmethoxy)phenyl](2-thienyl)}-3-methylbenzoic acid;
(y) 4-{4-[2-(phenylmethoxy)phenyl]-3-thienyl}benzoic acid;
(z) (4-{4-[2-(phenylmethoxy)phenyl](3-thienyl)}phenyl)-N-(3-pyridylmethyl)formamide;
(aa) 4-[3-(2-{[4-(difluoromethoxy)phenyl]methoxy}-5-chlorophenyl)(2-thienyl)]-3-methylbenzoic acid;
(ab) 4-(3-{2-[(4-carboxyphenyl)methoxy]-5-chlorophenyl}-2-thienyl)benzoic acid;
(ac) 3-(3-{2-[(4-carboxyphenyl)methoxy]-5-chlorophenyl}-2-thienyl)benzoic acid;
(ad) 4-(3-{5-chloro-2-[(2-chloro-4-fluorophenyl)methoxy]phenyl}(2-thienyl))-3-methylbenzoic acid; and
(ae) [4-(3-{5-chloro-2-[(2-chloro-4-fluorophenyl)methoxy]phenyl}(2-thienyl))-3-methylphenyl]-N-(3-pyridylmethyl)formamide, or a pharmaceutically acceptable salt or ester thereof.

11. A compound selected from the group consisting of:

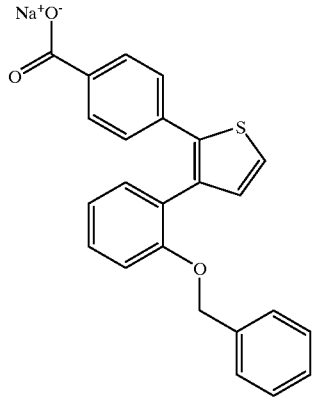

-continued

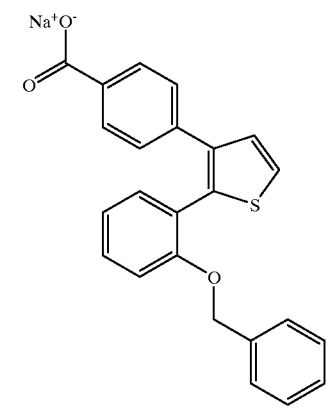

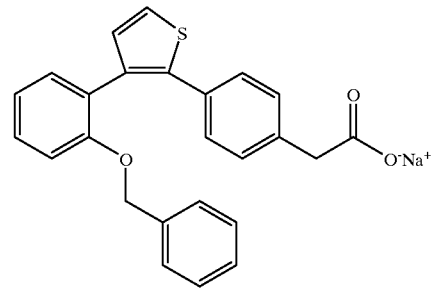

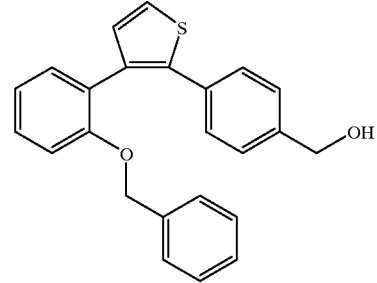

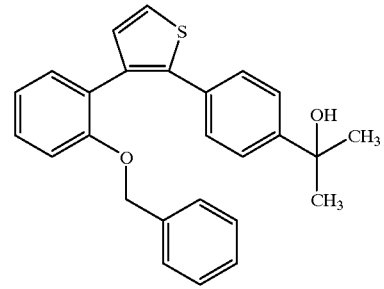

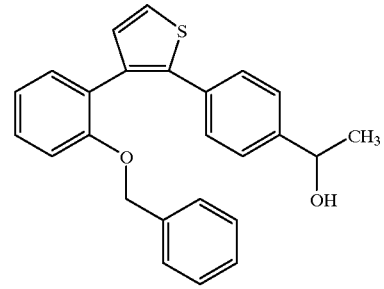

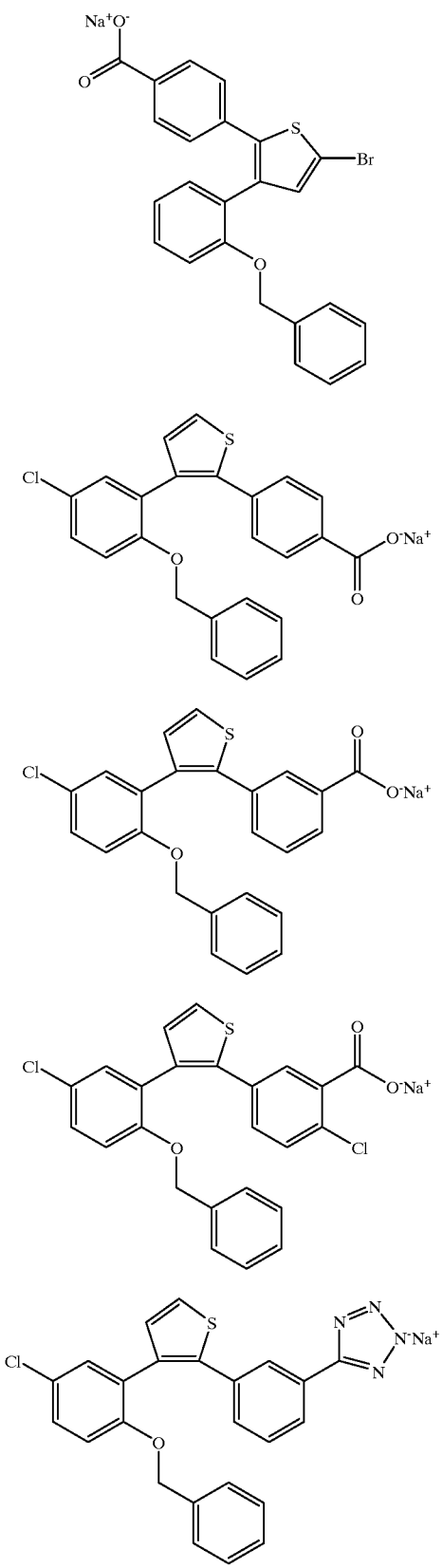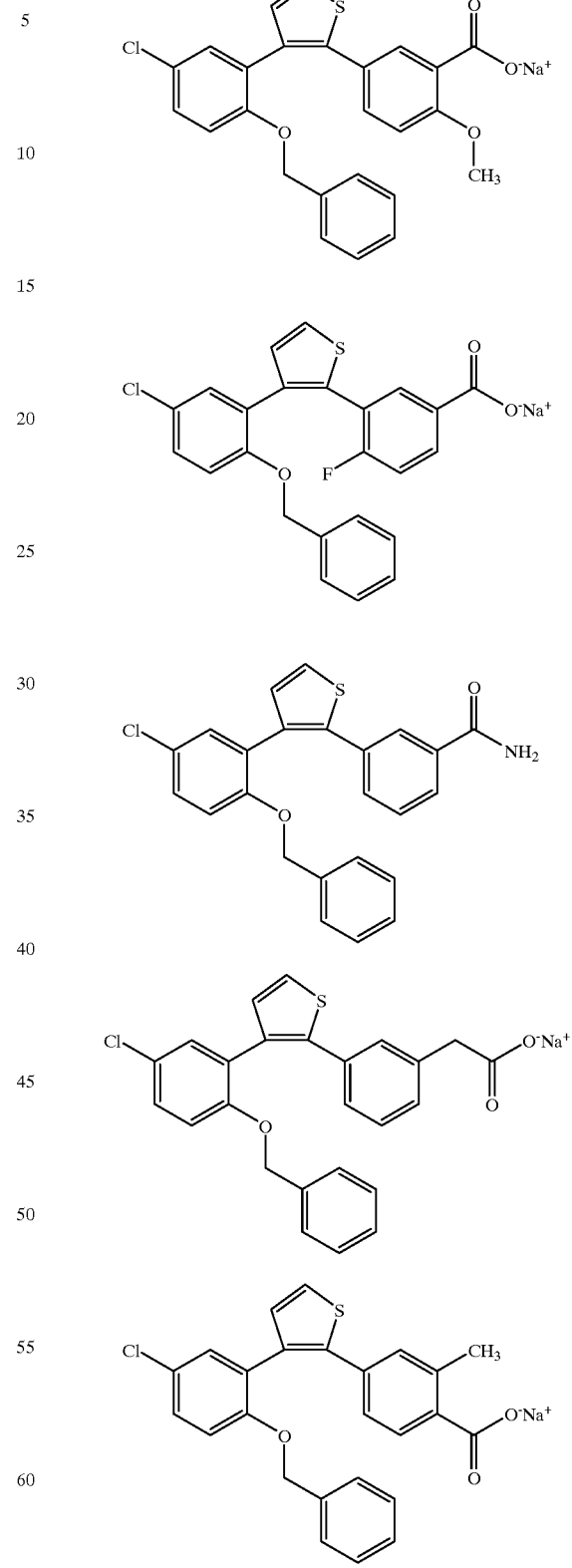

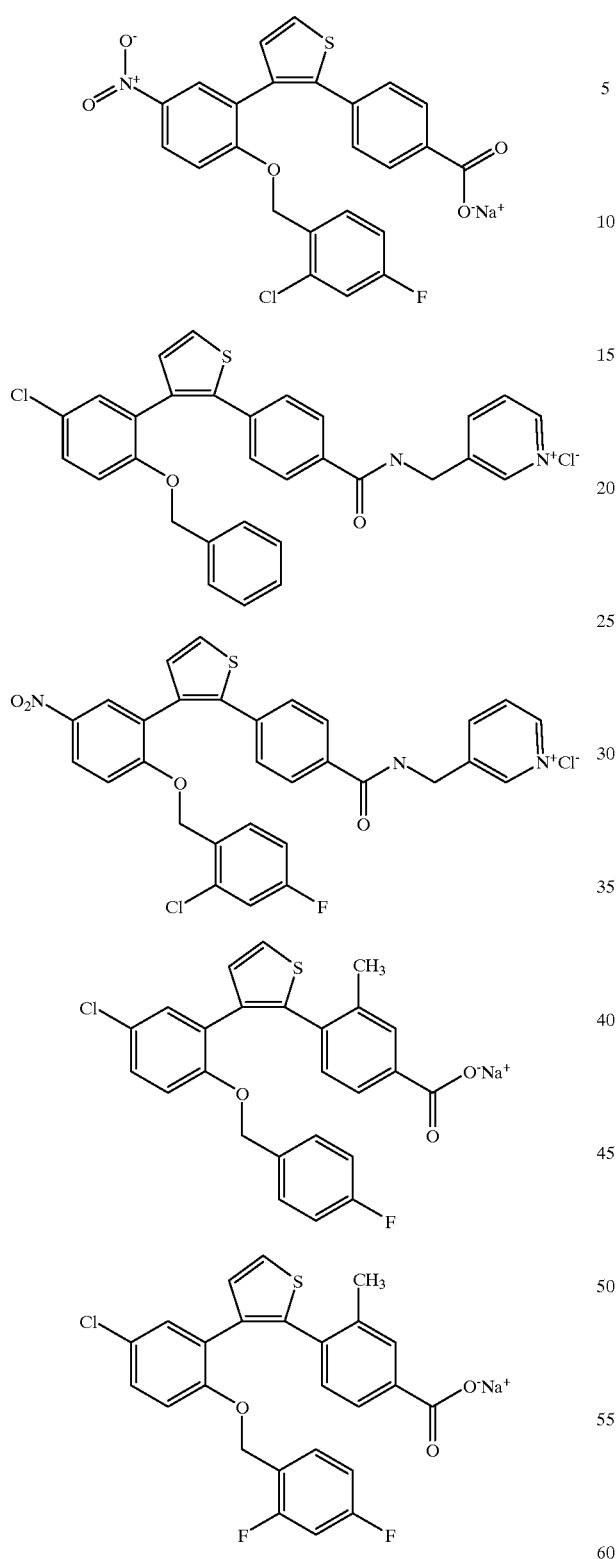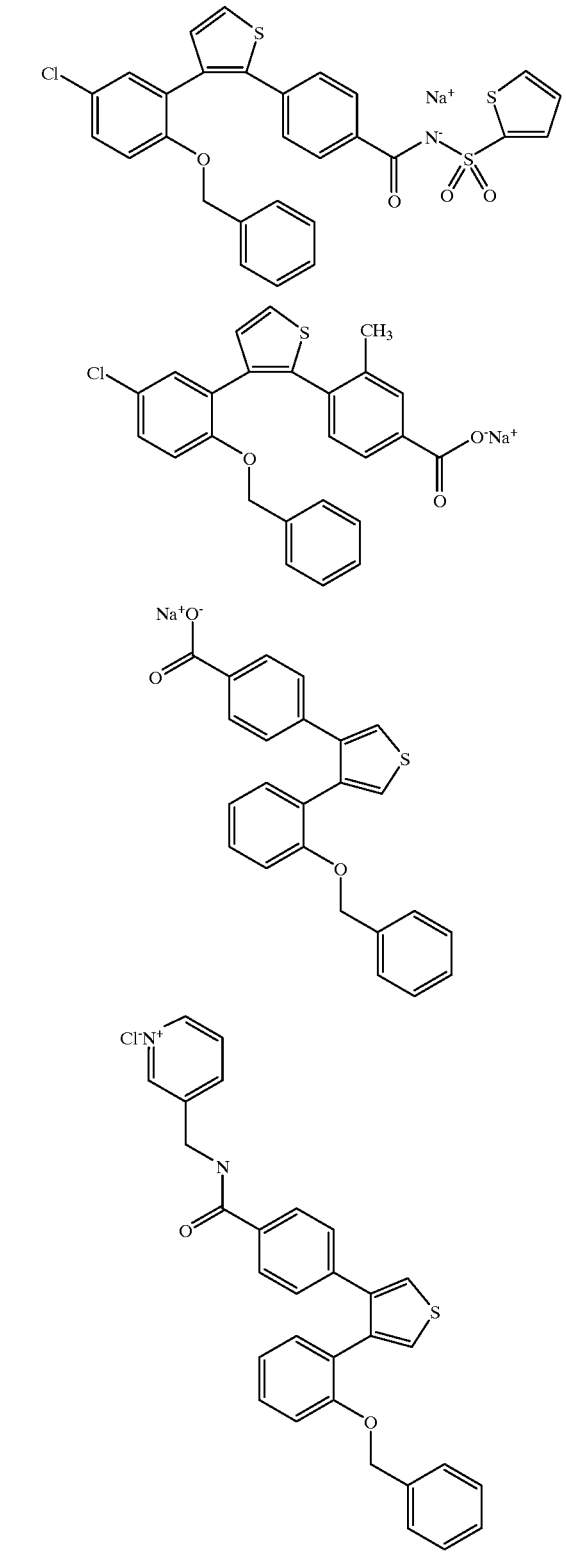

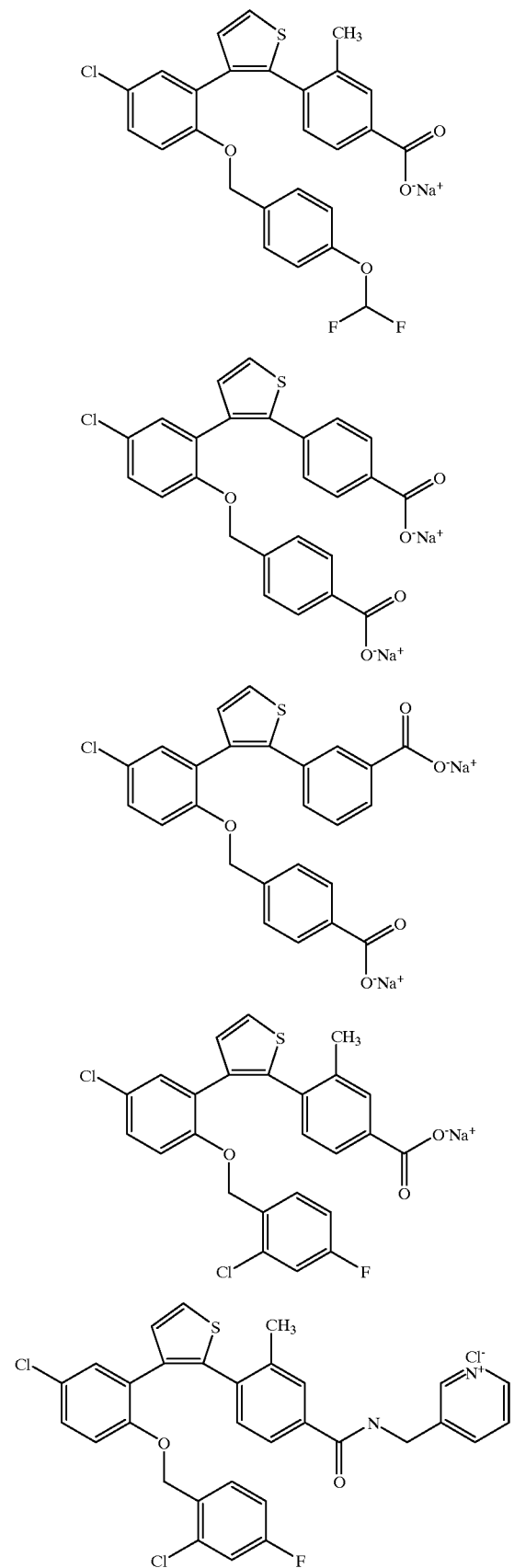

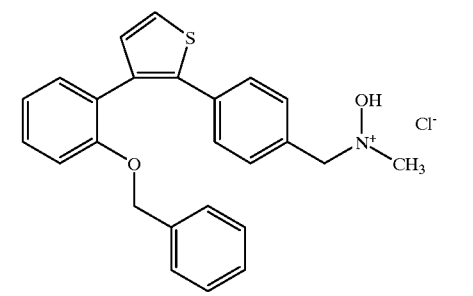
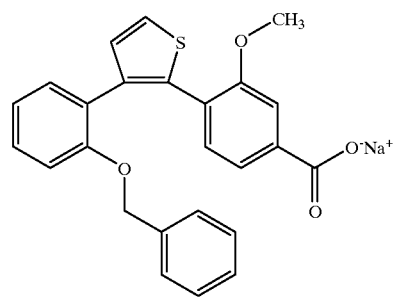
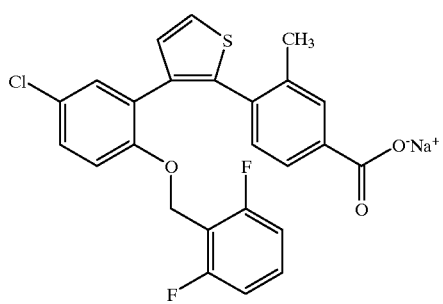
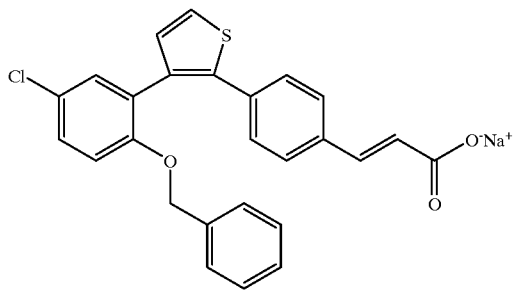
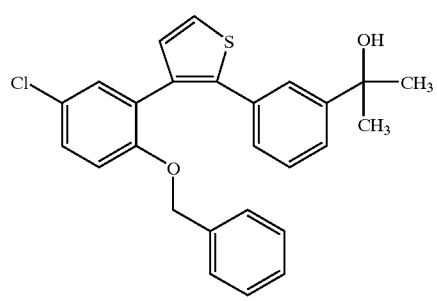
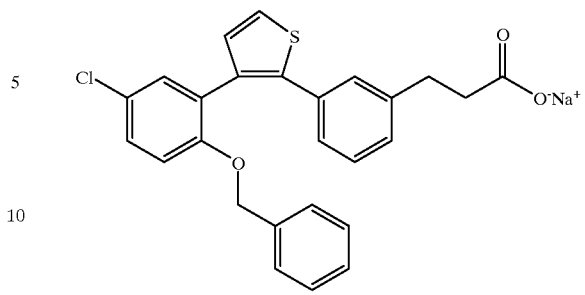
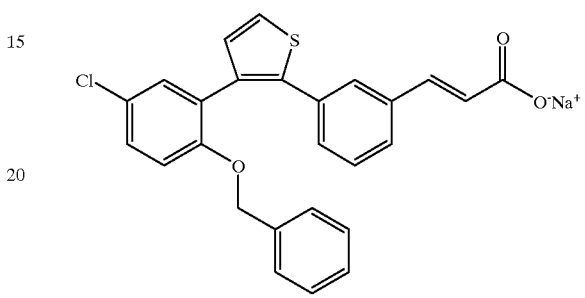
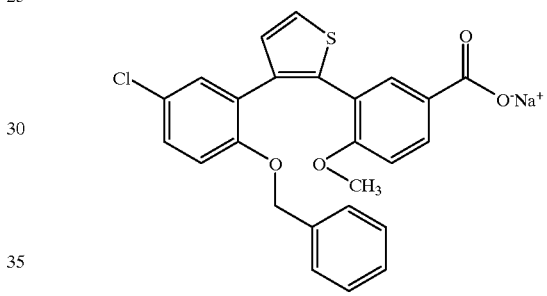
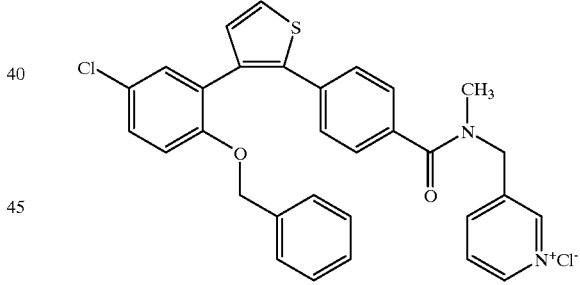
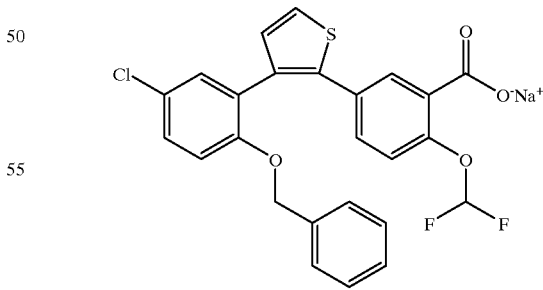

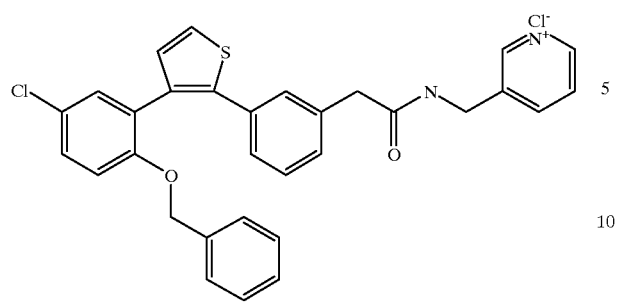
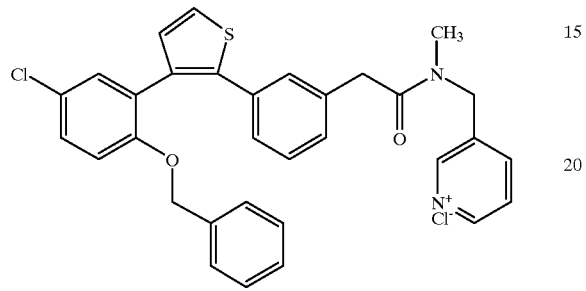
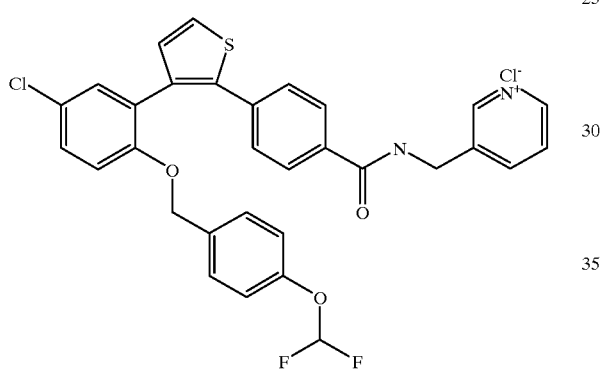
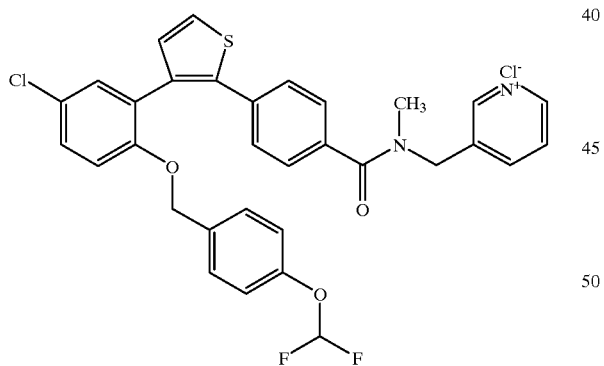
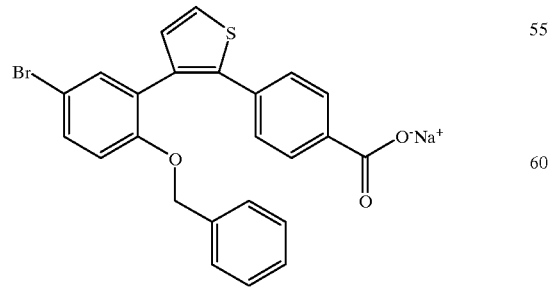
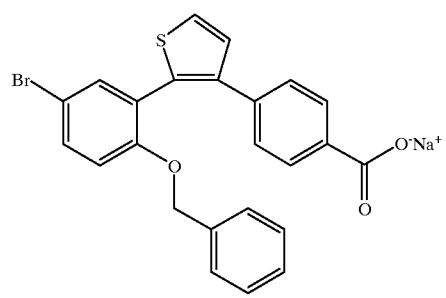
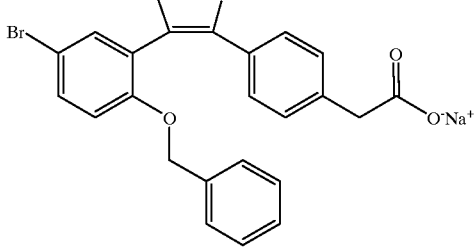
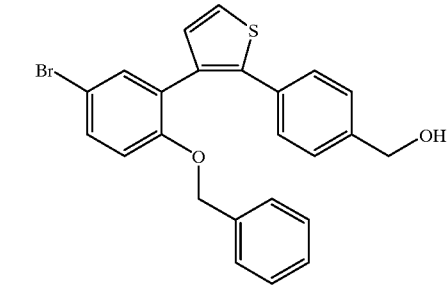
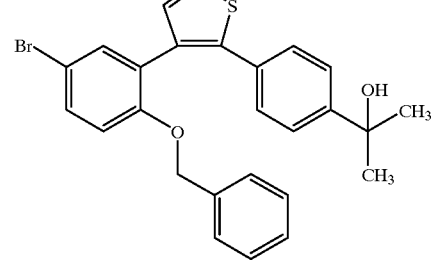
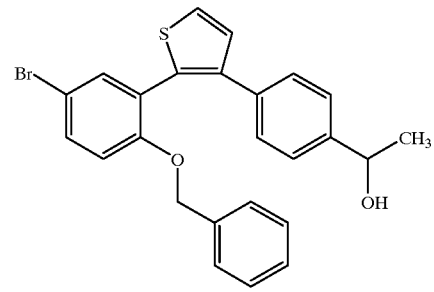

-continued
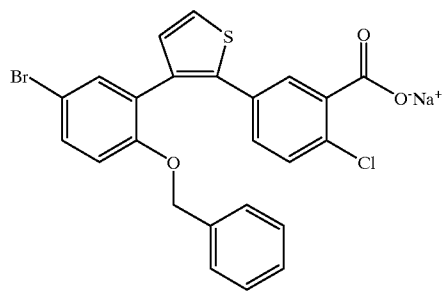
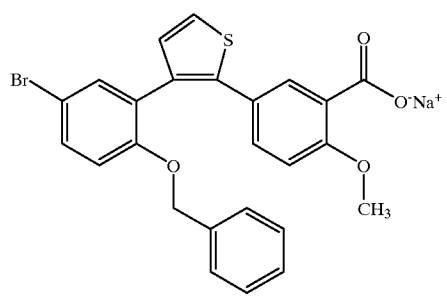
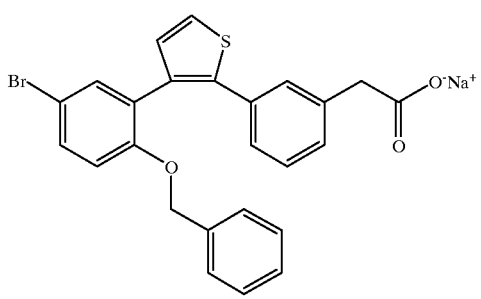
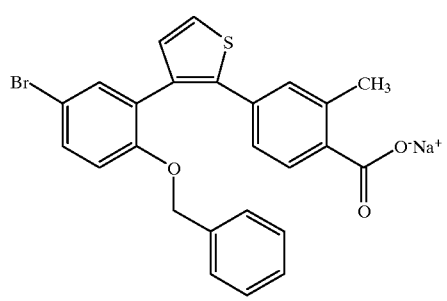
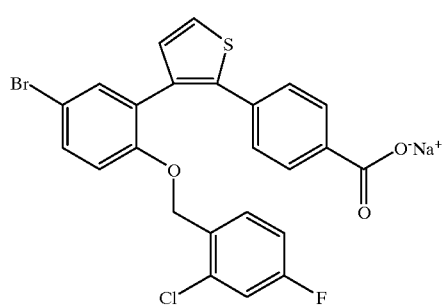
-continued
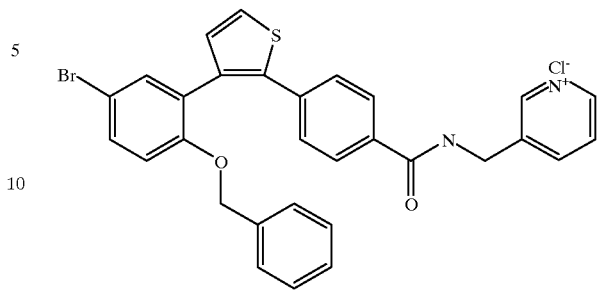
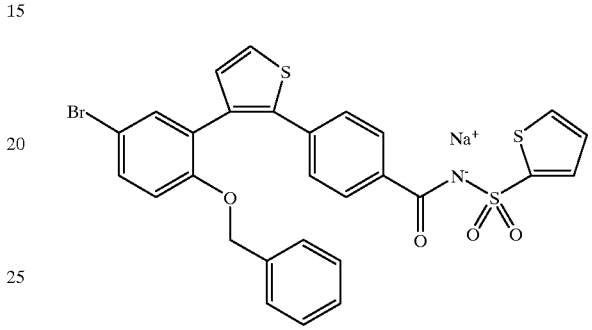
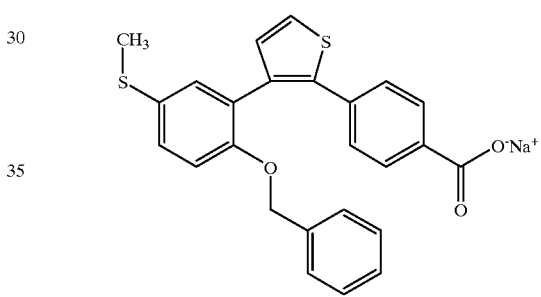
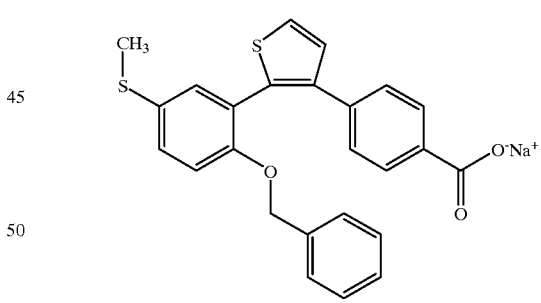
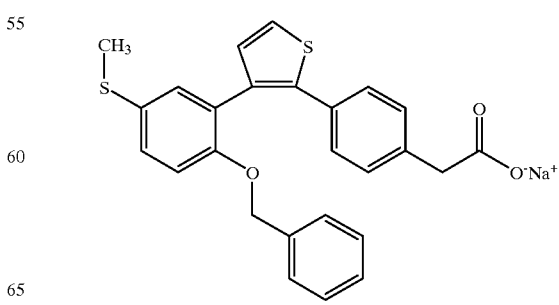

-continued

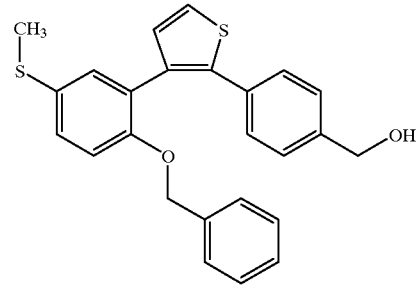

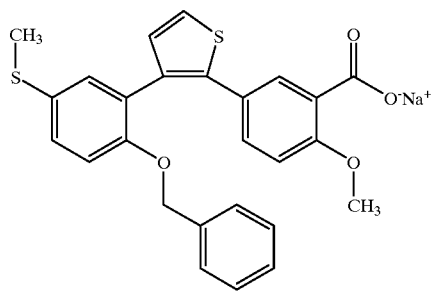

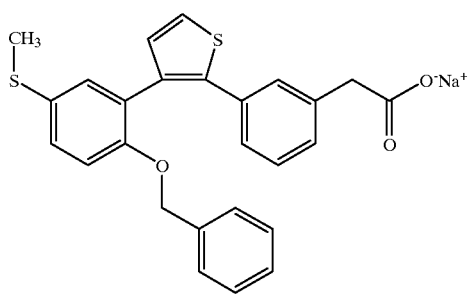

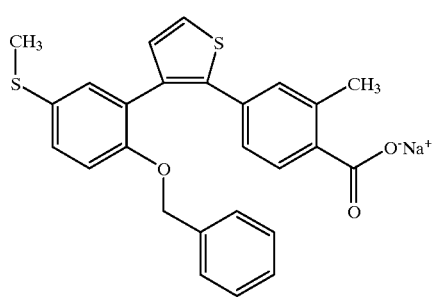

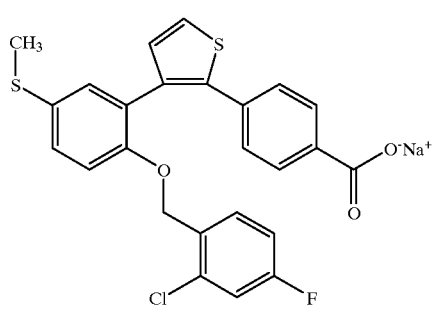

-continued

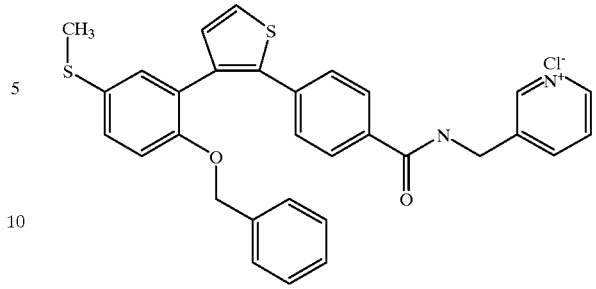

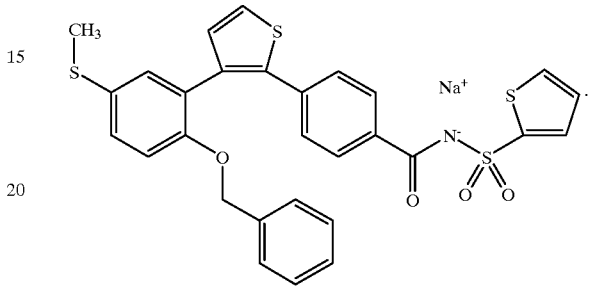

12. A pharmaceutical composition comprising a compound according to claim 1 in combination with a pharmaceutically acceptable carrier.

13. A method of treating a prostaglandin mediated disease comprising administering to a mammalian patient in need of such treatment a compound according to claim 1 in an amount which is effective for treating a prostaglandin mediated disease.

14. A method according to claim 13 wherein the prostaglandin mediated disease is selected from the group consisting of:

(1) pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, rheumatoid arthritis, degenerative joint diseases (osteoarthritis), gout and ankylosing spondylitis, bursitis, burns, radiation and corrosive chemical injuries, sunburns, pain following surgical and dental procedures as well as immune and autoimmune diseases;

(2) cellular neoplastic transformations or metastic tumor growth;

(3) diabetic retinopathy and tumor angiogenesis;

(4) prostanoid-induced smooth muscle contraction associated with dysmenorrhea, premature labor, asthma or eosinophil related disorders;

(5) Alzheimer's disease;

(6) glaucoma;

(7) bone loss;

(8) osteoporosis;

(9) promotion of bone formation;

(10) Paget's disease;

(11) cytoprotection in peptic ulcers, gastritis, regional enteritis, ulcerative colitis, diverticulitis or other gastrointestinal lesions;

(12) GI bleeding and patients undergoing chemotherapy;

(13) coagulation disorders selected from hypoprothrombinemia, haemophilia and other bleeding problems;

(14) kidney disease;

(15) thrombosis;

(16) occlusive vascular disease;

(17) presurgery; and

(18) anti-coagulation.

15. A method according to claim 14 wherein the prostaglandin mediated disease is selected from the group consisting of: pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, rheumatoid arthritis, degenerative joint diseases (osteoarthritis), gout and ankylosing spondylitis, bursitis, burns, radiation and corrosive chemical injuries, sunburns, pain following surgical and dental procedures as well as immune and autoimmune diseases.

16. A method according to claim 15 wherein the prostaglandin mediated disease is pain, fever or inflammation associated with dysmenorrhea.

17. A method according to claim 14, wherein the compound is co-administered with other agents or ingredients.

18. A method according to claim 17 wherein the compound is co-administered with another agent or ingredient selected from the group consisting of:

(1) an analgesic selected from acetaminophen, phenacetin, aspirin, a narcotic;

(2) a cyclooxygenase-2 selective nonsteroidal anti-inflammatory drug or a conventional nonsteroidal anti-inflammatory drug;

(3) caffeine;

(4) an $H_2$-antagonist;

(5) aluminum or magnesium hydroxide;

(6) simethicone;

(7) a decongestant selected from phenylephrine, phenylpropanolamine, pseudophedrine, oxymetazoline, ephinephrine, naphazoline, xylometazoline, propylhexedrine, or levo-desoxyephedrine;

(8) an antiitussive selected from codeine, hydrocodone, caramiphen, carbetapentane and dextramethorphan;

(9) another prostaglandin ligand selected from misoprostol, enprostil, rioprostil, ornoprostol and rosaprostol; a diuretic; and

(10) a sedating or non-sedating antihistamine.

19. A method according to claim 17 wherein the compound is co-administered with a cyclooxygenase-2 selective nonsteroidal anti-inflammatory drug or a conventional nonsteroidal anti-inflammatory drug.

20. A method according to claim 17 wherein the compound is co-administered with a conventional nonsteroidal anti-inflammatory drug selected from the group consisting of: aspirin, ibuprofen, naproxen, and ketoprofen.

21. A method according to claim 19 wherein the compound is co-administered with a cyclooxygenase-2 selective nonsteroidal anti-inflammatory drug selected from rofecoxib and celecoxib.

* * * * *